United States Patent [19]

Lang et al.

[11]  4,346,088
[45]  Aug. 24, 1982

[54] THIAZOLINE DERIVATIVES

[75] Inventors: Hans-Jochen Lang, Hofheim am Taunus; Bernhard Seuring, Frankfurt am Main; Ernold Granzer, Kelkheim, all of Fed. Rep. of Germany

[73] Assignee: Hoechst Aktiengesellschaft, Frankfurt am Main, Fed. Rep. of Germany

[21] Appl. No.: 165,218

[22] Filed: Jul. 1, 1980

[30] Foreign Application Priority Data

Jul. 3, 1979 [DE] Fed. Rep. of Germany ....... 2926771

[51] Int. Cl.³ .................. A61K 31/425; C07D 277/38; C07D 417/12
[52] U.S. Cl. .......................... 424/248.51; 260/245.5; 260/544 S; 424/250; 424/251; 424/267; 424/270; 544/63; 544/96; 544/133; 544/237; 544/333; 544/367; 546/209; 548/197; 562/430
[58] Field of Search .......... 548/197; 424/270, 248.51, 424/250, 267, 251; 544/133, 367, 96, 63, 237, 333; 546/209; 260/245.5

[56] References Cited
U.S. PATENT DOCUMENTS

| | | | |
|---|---|---|---|
| 4,061,647 | 12/1977 | Lang et al. | |
| 4,061,761 | 12/1977 | Lang et al. | 260/245.5 |
| 4,083,979 | 4/1978 | Lang et al. | |
| 4,118,501 | 10/1978 | Lang et al. | 260/245.5 |

FOREIGN PATENT DOCUMENTS 2533821 2/1977 Fed. Rep. of Germany .
2546165 4/1977 Fed. Rep. of Germany .

Primary Examiner—Alton D. Rollins
Attorney, Agent, or Firm—Curtis, Morris & Safford

[57] ABSTRACT

Thiazoline derivatives of the general formula I

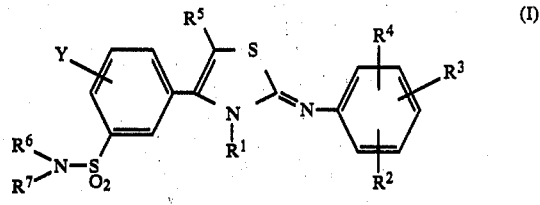

wherein $R^1$ to $R^7$ have the specified meanings, physiologically acceptable acid addition salts thereof, processes for their preparation, pharmaceutical preparations based on these compounds and their use for acting on the serum lipoprotein spectrum. The invention moreover relates to compounds of the formulae

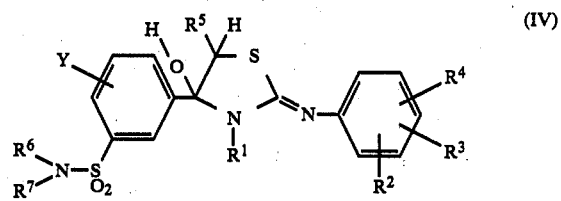

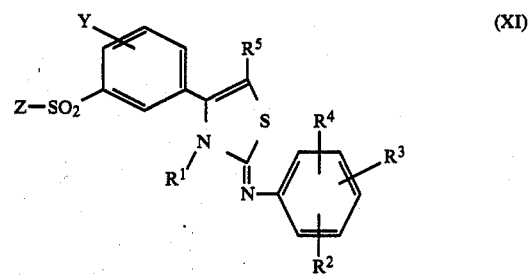

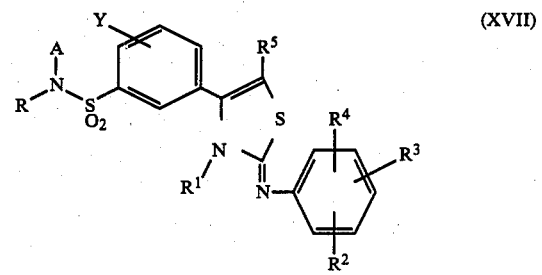

wherein A, R, $R^1$ to $R^7$, Y and Z have the specified meanings.

13 Claims, No Drawings

THIAZOLINE DERIVATIVES

The invention relates to compounds of the general formula I

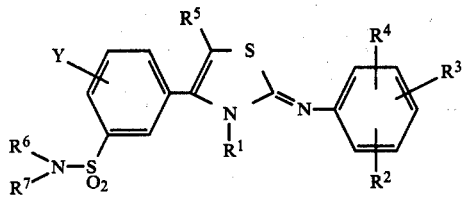

which, in the free form or in the form of their pharmacologically acceptable acid addition salts, possess valuable pharmacological properties and are therefore suitable as medicaments. In the formula: $R^1$ denotes $C_1$–$C_8$-alkyl, cycloalkyl having 3 to 8 C atoms or alkenyl having 3 to 4 C atoms, $R^2$, $R^3$ and $R^4$ are identical or different and denote hydrogen, halogen, alkyl or alkoxy each having 1 to 4 C atoms, methylenedioxy, ethylenedioxy, dimethyl- or diethylamino or trifluoromethyl, $R^5$ denotes hydrogen or alkyl having 1 to 3 C atoms, $R^6$ denotes hydrogen, or alkyl having 1 to 6 C atoms and $R^7$ denotes hydrogen, alkyl having 1 to 12 C atoms, cycloalkyl having 3 to 12 C atoms, allyl, phenylethyl or a benzyl radical

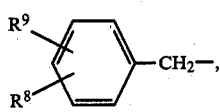

in which $R^8$ and $R^9$ are identical or different and denote hydrogen, methyl, chlorine or methoxy, or $R^6$ and $R^7$ are bonded via an alkylene chain, which can be branched and has a total of 8 C atoms and in which one methylene group can be replaced by a O atom or a N—CH$_3$ group, and Y denotes hydrogen, halogen or alkyl having 1 to 3 C atoms.

The invention further relates to a process for the preparation of the compounds of the general formula I, which comprises
(a) reacting compounds of the general formula II

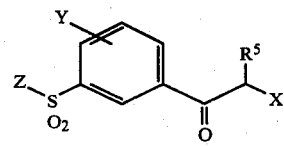

in which $R^5$ and Y are as defined, Z represents halogen or $R^6R^7N$—, in which $R^6$ and $R^7$ are as defined, and X is a leaving group, such as halogen, $CH_3SO_2$—O— or

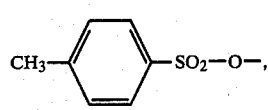

under the conditions for a condensation reaction, with a thiourea of the general formula III

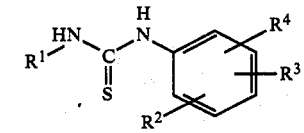

in which $R^1$ to $R^4$ are as defined, and, if Z represents halogen, subsequently reacting a resulting compound of the formula XI

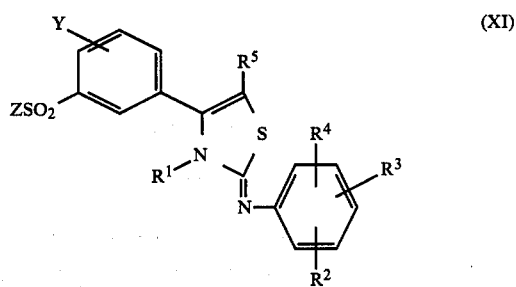

in which $R^1$, $R^2$, $R^3$, $R^4$, $R^5$ and Y are as defined under formula I and Z represents halogen, with an amine of the general formula $HNR^6R^7$, in which $R^6$ and $R^7$ are as defined, or
(b) splitting off water from compounds of the general formula IV

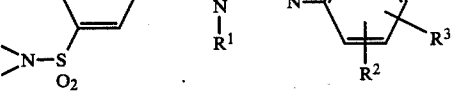

in which $R^1$ to $R^7$ and Y are as defined, or
(c) reacting compounds of the general formula V

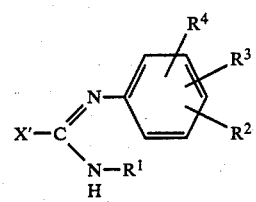

with compounds of the general formula VI

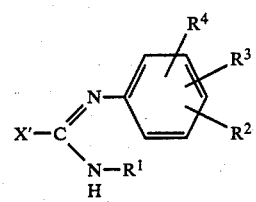

in which formulae $R^1$ to $R^7$ are as defined and X' is a leaving group, such as, for example, halogen, methoxy or methylthio, or
(d) reacting compounds of the formula V with carbodiimides VII

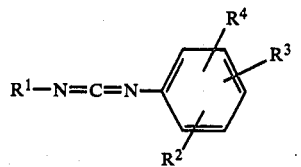

(VII)

in which $R^1$ to $R^4$ are as defined, or
(e) treating compounds of the general formula VIII

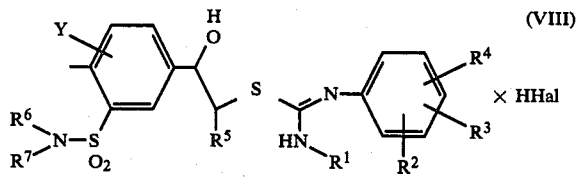

(VIII)

in which $R^1$ to $R^7$ and Y are as defined and Hal represents chlorine or bromine, with an oxidizing agent, or
(f) reacting compounds of the general formula IX

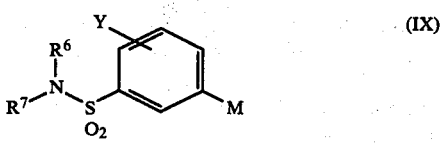

(IX)

in which $R^6$ and $R^7$ do not represent hydrogen and Y does not represent bromine or iodine, but these radicals are otherwise as defined above, and M represents lithium or a MgBr group, with compounds of the general formula X

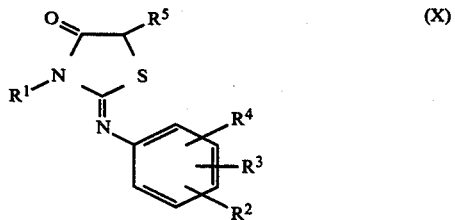

(X)

in which $R^1$ to $R^5$ are as defined, and subjecting the resulting reaction product to hydrolysis and dehydration,
and, if desired, converting the compounds of the general formula I in which $R^6$ and/or $R^7$ denote hydrogen, which compounds are obtained by route (a) to (f), by conventional alkylation into compounds in which $R^6$ and/or $R^7$ have one of the other meanings defined above, and, if desired, converting a resulting compound of the formula I into its acid addition salts, using organic or inorganic acids of the general formula H—A, or converting resulting salts of the compounds of the general formula I into the free basic compounds of the formula I, using bases.

Inorganic acids H—A which can be used are, for example: hydrogen halide acids, such as hydrochloric acid and hydrobromic acid, and also sulfuric acid, phosphoric acid and amidosulfonic acid.

Organic acids H—A which may be mentioned are, for example, methanesulfonic acid, ethanesulfonic acid, benzenesulfonic acid and p-toluenesulfonic acid.

The compounds of the formulae IV and XI are novel. The invention therefore further relates to compounds of the formula IV

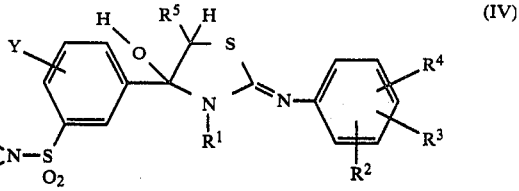

(IV)

in which $R^1$ to $R^5$ and Y are as defined under formula I, and the acid addition salts thereof. These are suitable as precursors for the preparation of compounds of the general formula I.

The invention also relates to compounds of the general formula XI

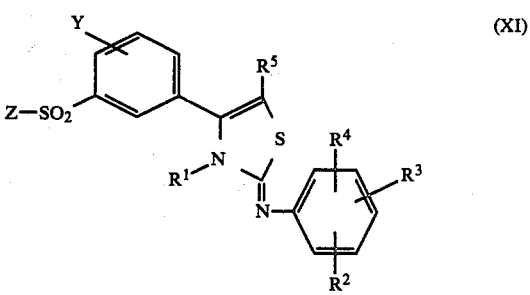

(XI)

in which $R^1$ to $R^5$ and Y are as defined under formula I and Z represents halogen, and the acid addition salts thereof, which can be used as intermediates in the preparation of compounds of the general formula I in accordance with procedure (a).

The compounds, according to the invention, of the formula I can also exist in their possible isomeric structures, but for the sake of simplicity only one of the possible isomeric forms of a particular substance is indicated.

The procedure designated under (a) is advantageously carried out by reacting the compounds II with the thioureas III in a molar ratio of 1:1 to 1:15. In general, no significant advantages are achieved by the use of larger molar excesses of thiourea.

The reaction is advantageously carried out in inert polar organic solvents, such as dimethylformamide, dimethylacetamide, ethylene glycol monomethyl ether or ethylene glycol dimethyl ether, and particularly advantageously is carried out in strongly polar protic solvents, such as methanol, ethanol, isopropanol, n-butanol, acetic acid, propionic acid or formic acid, or in mixtures of the said solvents with water; anhydrous mixtures of the said solvents are also suitable. The reaction can also be carried out without the use of a solvent, by warming the reaction mixture to a temperature range between 80° and 220° C., preferably between 100° and 180° C. When a solvent is used, the reaction is carried out in a preferred temperature range of 60° to 150° C.

The reaction time is to a large extent dependent on the solvent and on the reaction temperature employed and in general is between 15 minutes and 24 hours. The quantitative course of reaction to give the compounds I according to the invention is advantageously followed by thin layer chromatography on silica gel plates.

In many cases, the compounds I according to the invention separate out in the course of the reaction in the form of their acid addition salts, which are sparingly soluble and can be filtered off; if this is not the case, the solvent is evaporated and, if appropriate, the yield can be increased by the subsequent addition of a suitable precipitating agent, such as, for example, ethyl acetate, diethyl ether, diisopropyl ether, acetone or acetonitrile.

If Z in the general formula II denotes halogen, preferably chlorine, the resulting compounds of the formula XI are reacted with ammonia or an amine $HNR^6R^7$ to give the compounds I. Either aqueous solutions of ammonia and of the amines or liquid ammonia or the pure amines in excess can be used for this reaction, the excess ammonia or amine at the same time acting as the solvent. The reaction can also be carried out in organic solvents, such as, for example, dimethylformamide, dimethylacetamide, dimethylsulfoxide, dioxan, tetrahydrofuran or diethylene glycol dimethyl ether; particularly suitable solvents are, however, lower alcohols having 1 to 4 C atoms, such as, for example, methanol, ethanol or isopropanol. Theoretically, one mole of ammonia or amine in the presence of two moles of an auxiliary base are required for the conversion of the sulfonyl chlorides XI to the sulfonamides I. Accordingly, the procedure followed for the reaction can be to use at least 3 moles of ammonia or amine per mole of sulfonyl chloride XI. For this reaction, the use of 3-7 moles of ammonia or amine per mole of sulfonyl chloride is advantageous, but it is possible to use an even larger excess of amine. It is also possible to carry out the reaction with one or two moles of ammonia or amine, if the reaction is carried out in the presence of an auxiliary base, and in this case about 1-6 mole equivalents of the auxiliary base are used. Suitable auxiliary bases are inorganic and organic hydroxides, carbonates and bicarbonates, and also salt solutions of weak inorganic and organic acids, and in all cases tertiary amines, such as, for example, triethylamine, tri-n-butylamine, methyl-dicyclohexylamine or ethyldicyclohexylamine, are particularly advantageous. If used in excess, the tertiary amine can likewise serve as the reaction medium, without the addition of a further solvent. The reaction proceeds exothermically, so that, advantageously, the reaction mixture is cooled and the reaction is carried out at temperatures between −35° and +100° C., preferably between +10° and +60° C. The reaction time should be at least 30 minutes and the reaction can be discontinued at the latest after two days, no significant advantages being achieved with longer reaction times. A reaction time of between 6 and 20 hours is preferred. The procedure employed for working up is, advantageously, to dilute with water, after distilling off the amine and concentrating the reaction mixture if necessary, whereupon the compounds I precipitate, as sparingly soluble compounds.

If $R^6$ or $R^7$ in the compound I prepared in this way denotes a hydrogen atom, the pH should, as far as possible be adjusted to 7.5 to 8.5.

The compounds of the formula XI can be obtained from compounds of the formula XII, or salts thereof,

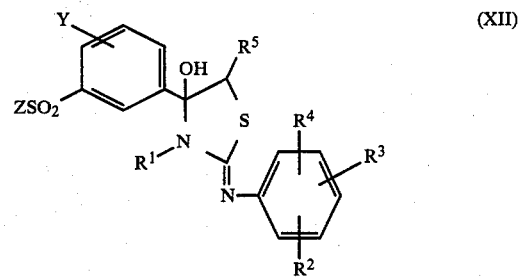

in which $R^1$ to $R^5$, X, Y and Z are as defined under formula XI, by the elimination of water.

This reaction is carried out under the conditions given under procedure (b), and is preferably carried out in glacial acetic acid or in solvents which distil as an azeotrope with water, such as methylene chloride, chloroform, dichloroethane, chlorobenzene, nitrobenzene, nitromethane, toluene or xylene, and, appropriately, the water formed during the reaction is determined by analysis. Advantageously, the reaction is carried out in the boiling solvents. Particularly advantageously, the compounds XI are obtained by heating the dry compounds XII to temperatures of 100° to 250° C. and preferably of 150° to 220° C. Appropriately, the water of condensation, which interferes, is removed by distilling off rapidly, preferably in a stream of air, or by applying an effective vacuum and using a desiccant.

The compounds of the formula XI, and their salts, can also be obtained from aniline derivatives XIII

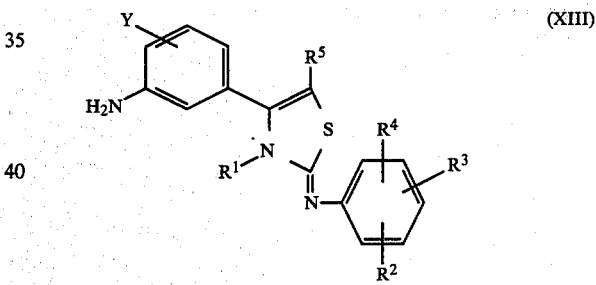

in a manner which is in itself known, by diazotizing and subsequently carrying out a Meerwein reaction. The compounds XIII can be prepared from aminoketones XIV, or their acid addition salts

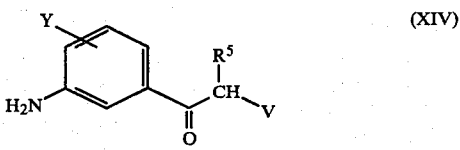

in which Y and $R^5$ are as defined and V represents H, by halogenation, preferably with elementary bromine or chlorine, and subsequent reaction of the halogenoketones XIV, in which V denotes Cl or Br, with a thiourea of the formula III under the conditions for carrying out procedure (a).

The majority of the thioureas III which are used are substances which have been described in the literature. They are prepared in a known manner, by reacting amines with isothiocyanates, carbon disulfide or thiophosgene (compare Houben-Weyl, "Methoden der organischen Chemie" ("Methods of Organic Chemistry"), Volume 9, page 384, 4th edition, Georg-Thieme-Verlag, Stuttgart, 1955).

The compounds of the general formula II can be obtained by several methods described in the literature (compare, for example, German Offenlegungsschrift No. 2,436,263).

In accordance with the procedure indicated under (b), 2-arylimino-4-hydroxy-4-(3-sulfamoylphenyl)-thiazolidines (IV) are dehydrated by the action of heat, preferably by proton catalysis, to give the compounds of the general formula I according to the invention. This reaction is advantageously carried out in polar organic solvents, suitable solvents being protic solvents, such as lower alcohols having 1 to 6 C atoms, for example methanol, ethanol, propanol, iso-propanol or 1- or 2-butanol, ethylene glycol monomethyl ether, diethylene glycol monomethyl ether or lower aliphatic carboxylic acids, such as acetic acid, propionic acid or formic acid, or mixtures of the said solvents. The use of water, especially as a mixture with the said solvents, is also advantageous.

Catalysts which can be used are inorganic or organic proton acids, such as hydrochloric acid, sulfuric acid, phosphoric acid, methanesulfonic acid, toluenesulfonic acid, one of the aliphatic carboxylic acids mentioned as a solvent, or an aromatic carboxylic acid, such as salicylic acid or benzoic acid. In principle, the dehydration of the compounds IV can also be carried out without the use of a catalyst and also without the use of a solvent.

The reaction is carried out in a temperature range between 0° and 200° C., lower temperatures resulting in long reaction times, and the danger of by-products being formed increasing at higher temperatures. Preferably, the reaction is carried out at between 50° and 150° C., and particularly advantageously the reaction is carried out in boiling methanol, ethanol, propanol or glacial acetic acid. The quantitative course of the reaction is appropriately followed by recording the thin layer chromatogram on silica gel plates.

Advantageously, the reaction mixture is worked up by a procedure analogous to that indicated under procedure (a).

The compounds of the general formula IV are obtained by methods which are in themselves known, for example by procedures analogous to those indicated in German Offenlegungsschrift No. 2,436,263. Reaction conditions which are as mild as possible and reaction temperatures and working-up conditions below 40° C. should be chosen if it is desired to prepare compounds of the formula IV which are as pure as possible. In accordance with procedure (c), compounds of the general formula V are reacted with compounds of the formula VI, advantageously in a polar organic solvent, such as, for example, in lower alcohols having 1 to 4 C atoms, ethylene glycol monomethyl ether or ethylene glycol dimethyl ether, diethylene glycol monomethyl ether or diethylene glycol dimethyl ether, acetone, ethyl acetate or dimethylformamide.

The reaction is advantageously carried out at between 0° and 80° C., preferably between 15° and 40° C., and, after the exothermic reaction has subsided, the reaction mixture is heated to temperatures between 60° and 140° C. in order to bring the formation of the compounds of the formula I to completion. The course of the reaction is appropriately followed by thin layer chromatography on silica gel plates. The reaction time is between 5 and 60 hours. Compounds V which prove particularly suitable for this reaction are, in particular, those which carry, on the sulfamoyl group, a bulky organic radical $R^7$, such as, for example, tert.-butyl, as well as hydrogen as $R^6$, or those compounds V in which $R^6$ and $R^7$ carry an organic radical as a substituent.

In order to carry out procedure (d), the mercaptoketones of the formula V are reacted in an anhydrous, polar, inert solvent, such as, for example, in methyl acetate, ethyl acetate, dioxan or tetrahydrofuran, with the carbodiimides of the general formula VII in a molar ratio of 1:1. The reaction is carried out in a temperature range between 0° and 40° C., preferably between 10° and 30° C. After the weakly exothermic reaction has subsided, the reaction mixture is stirred for about 10–20 hours at 20° to 40° C. After adding an equal amount by volume of a protic solvent, preferably methanol, ethanol, propanol, isopropanol, n-butanol, glacial acetic acid or water, or also mixtures of the said solvents, the reaction mixture is heated at temperatures between 60° and 140° C. for a further 2 to 70 hours. The course of the reaction is appropriately followed by thin layer chromatography on silica gel plates.

The compounds of the formula V which are used in procedures (c) and (d) can be prepared by methods known from the literature (for example German Offenlegungsschrift No. 2,436,263). The preparation of compounds of the general formulae VI and VII is also described in the literature (for example Chem. Ber. 97, 1232 (1964), Bull.Chem.Soc.Jap. 46, 1765 (1973), Angew.Chem. 74, 214 (1962) and Bull.Soc.Chim. Jap. 38, 1806 (1965)).

In accordance with procedure (e), the compounds of the general formula VIII are converted to the compounds of the formula I using a suitable oxidizing agent, preferably using active manganese-IV oxide. The solvents used are preferably halogenated hydrocarbons, such as, for example, methylene chloride, chloroform or tetrachloroethane, but particularly preferentially acetonitrile or mixtures of the said solvents with acetonitrile. The reaction is carried out in a temperature range between 0° and 40° C., preferably between 20° and 30° C., over a period of 10 to 60 hours, the oxidizing agent is then filtered off and, in order to bring the reaction to completion, the reaction mixture is heated, after adding an equal volume of a protic solvent such as methanol, ethanol, propanol, isopropanol, butanol or glacial acetic acid, for 1 to 30 hours at temperatures between 60° and 140° C.

Compounds of the general formula VIII are obtained by a procedure analogous to that described in German Offenlegungsschrift No. 2,436,263, by reacting compounds of the general formula XV

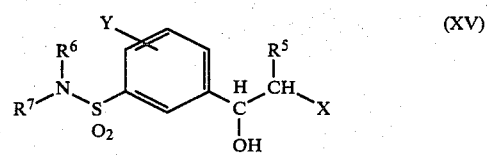

(XV)

in which the substituents X, Y and $R^5$ to $R^7$ are as defined, with thioureas of the general formula III.

According to procedure (f), compounds of the general formula IX, in which Y does not represent bromine or iodine and in which $R^6$ and $R^7$ differ from hydrogen, are reacted with the compounds of the formula X. The compounds IX and X are advantageously reacted in a molar ratio of 1:1 to 1:1.5 in an inert and anhydrous solvent customary for metal-organic reactions, preferably in tetrahydrofuran, in a preferred temperature range between −30° and +60° C. After the reaction has ended, the reaction products are hydrolyzed in a manner customary for metal-organic reactions; for example, the reaction mixture is introduced at temperatures between −5° and +20° C. into an aqueous, saturated ammonium chloride solution, whilst maintaining a pH range of 6 to 8. In order to bring the conversion to the compounds I according to the invention to completion, the hydrolysis mixture can be warmed to temperatures of 40°-100° C., preferably of 60°-80° C., whilst monitoring the progress of the reaction by thin layer chromatography. Advantageously, however, the product mixture which has not yet been completely converted into the compounds I is worked up by filtration or extraction with a suitable solvent, such as methyl acetate, ethyl acetate or nitromethane, and is then treated in accordance with procedure (b).

Methods of preparation for the compounds IX and also their precursors are described in the literature (for example German Offenlegungsschrift No. 2,436,263).

The compounds of the formula X are obtained, for example, in a known manner by reacting α-halogenocarboxylic acid esters XVI, in which $B=OR^8$,

(XVI)

in which $R^5$ and X are as defined and $R^8$ is preferably phenyl or lower alkyl, such as methyl or ethyl, with thioureas of the general formula III. Correspondingly, α-halogenocarboxylic acids (B=OH) and α-halogenocarboxylic acid chlorides (B=Cl) are also suitable.

The compounds of the formula I can be reversibly reacted in a suitable solvent with an acid of the formula H—A. For this reaction, the compounds I can be introduced into the pure acids, preferably at temperatures between 0° and 60° C., if these are liquid or have a melting point not substantially higher than 60° C. and if they do not give rise to any side reactions. Advantageously, however, the reaction is carried out in a solvent, such as, for example, in water or in an organic solvent, such as, for example, in dioxan, tetrahydrofuran, ether, a lower alkyl acetate having 1 to 4 C atoms in the alkyl part, acetonitrile, nitromethane, acetone, methyl ethyl ketone or the like; lower alcohols having 1 to 4 C atoms and carboxylic acids having 2 to 4 C atoms have proved particularly suitable. 1-1.5 moles of the acids H—A are used per mole of the compounds I, but it is also possible to use larger amounts of acid. Appropriately, the reaction is carried out at temperatures between 0° and 120° C. and preferably between 10° and 60° C. The reaction is moderately exothermic.

When the reaction is carried out in aqueous solution, the compounds I in general dissolve immediately on addition of the acids H—A and only in rare cases do the corresponding acid addition compounds precipitate out. When a solution is obtained, the salts according to the invention are appropriately isolated by evaporating off the water under mild conditions, preferably by freeze-drying. When the reaction is carried out in organic solvents, the acid addition salts frequently precipitate as sparingly soluble compounds on the addition of the particular acid H—A. If a solution is obtained, the acid addition compounds are precipitated using a suitable precipitating agent, after prior concentration of the solution if necessary. Suitable precipitating agents are the solvents described for the same purpose in process (a).

The acid addition products are very frequently obtained in the form of viscous oils or amorphous glassy products, even in a very high degree of purity. These amorphous products can frequently be made to crystallize by treatment with an organic solvent, by warming to 40° to 80° C. if necessary. Suitable crystallization-promoting solvents are, in particular, lower alkyl acetates having 1 to 4 C atoms in the alkyl part, such as methyl acetate, ethyl acetate and n-butyl acetate, and also lower dialkyl ketones, such as acetone or methyl ethyl ketone, lower dialkyl ethers, such as diethyl ether, diisopropyl ether or di-n-butyl ether, and also acetonitrile and nitromethane, and in some cases also lower alcohols, such as methanol, ethanol, isopropanol or n-butanol.

The acid addition products can be deprotonated in a suitable solvent by treatment with bases, to give the compounds of the general formula I. Examples of bases which can be used are solutions of inorganic hydroxides, such as lithium hydroxide, sodium hydroxide, potassium hydroxide, calcium hydroxide or barium hydroxide, carbonates or bicarbonates, such as sodium carbonate, potassium carbonate, sodium bicarbonate or potassium bicarbonate, ammonia and amines, such as triethylamine, dicyclohexylamine, piperidine and methyldicyclohexylamine.

When the reaction is carried out in an aqueous medium, the free basic compounds I precipitate as sparingly soluble compounds and can be separated off and isolated by filtration or extraction with an organic solvent, preferably with ethyl acetate. Suitable organic reaction media are, in particular, lower alcohols having 1 to 4 C atoms, preferably methanol and ethanol, but it is also possible to use ethyl acetate, diethyl ether, tetrahydrofuran, dioxan, diethylene glycol dimethyl ether, dimethylformamide and others. The reaction to give the compounds I takes place spontaneously. The reaction is carried out at between −35° and 100° C., preferably between 0° and 60° C. If a water-miscible organic solvent is used, the free bases of the formula I are precipitated, after prior concentration of the reaction mixture if necessary, by adding water. If a water-immiscible solvent is used, the procedure employed is, advantageously, to wash the reaction mixture, after the reaction has taken place, with water and to evaporate off the organic solvent, optionally after prior drying.

If at least 1 mole of a sufficiently strong base is allowed to act on compounds of the formula I in which $R^6$ and/or $R^7$ denote hydrogen, deprotonation of the sulfonamide group takes place and salts of the general formula XVII

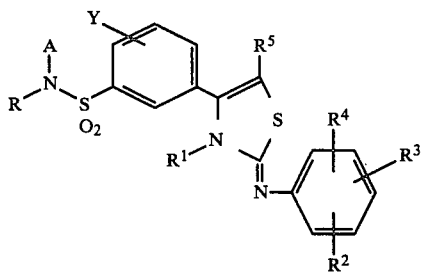
(XVII)

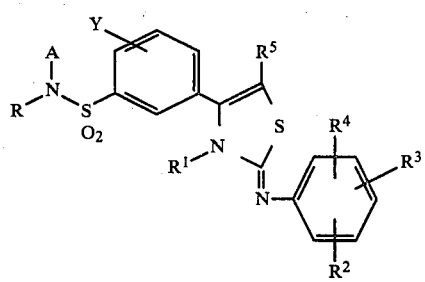
(XVII)

are obtained in which A is the cation of an alkali metal or alkaline earth metal and $R^1$ to $R^5$ and also Y are as defined and R has the meaning of $R^6$ or $R^7$.

Bases which can be used are hydroxides of the alkali metals and alkaline earth metals, preferably NaOH and KOH, alkali metal alcoholates and alkaline earth metal alcoholates, such as $NaOCH_3$ and $NaOC_2H_5$, NaH, sodium methylsulfinylmethide and the like.

The solvents used are water or polar organic solvents, such as methanol, ethanol, isopropanol, n-butanol, dimethylformamide, dimethylsulfoxide, diethylene glycol dimethyl ether or acetonitrile.

On the addition of one mole of a suitable acid H—A, the compounds I according to the invention are obtained again, and it is also possible to use ammonium salts as acids.

This reversible acid/base reaction can be used for purification of the compounds I. In addition, the salts XVII can be used in order to prepare compounds of the formula I which are correspondingly converted at the sulfonamide group by means of alkylation reactions.

Water can be used as the solvent for alkylation reactions. However, these reactions are preferably carried out in the polar organic solvents mentioned and particularly advantageously are carried out in a two-phase mixture of water and a water-immiscible organic phase, such as, for example, toluene, benzene, xylene, methylene chloride, chloroform, carbon tetrachloride, ethyl acetate or a mixture of the said solvents. The use of a phase transfer catalyst, such as, for example, tetra-n-butyl-ammonium chloride, benzyl-triethyl-ammonium chloride, benzyl-dimethyl-tetradecylammonium chloride, tetra-n-butylphosphonium chloride or dicyclohexyl-[18]crown-6, can also be advantageous. The reaction is carried out in a temperature range of $-20°$ to $+100°$ C., preferably between $+10°$ and $40°$ C., and the course of the reaction is followed by thin layer chromatography. Conventional alkylating agents of the general formula R—X are used, in which R has the meaning of $R^6$ or $R^7$ and X represents, for example, bromine, chlorine, iodine, —O—$SO_2$—OR, —O—$SO_2CH_3$ or

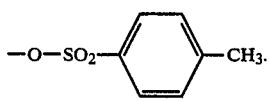

The salts XVII are advantageously produced without subsequent isolation in the indicated manner in the reaction mixture, by the action of one of the bases mentioned on the compounds I and subsequent or parallel addition of one of the alkylating agents R—X designated.

The compounds of the formula XVII in which $R^1$ to $R^5$ and Y are as defined under formula I, R has the meaning of $R^6$ or $R^7$ and A denotes the cation of an alkali metal or alkaline earth metal, are novel. The invention therefore also relates to these compounds. They are suitable, in particular, as intermediates in the alkylation of compounds of the formula I in which $R^6$ and/or $R^7$ denote hydrogen.

Preferred compounds according to the invention are those of the general formula I in which the substituents have the meanings described below in Table 1:

Table 1

$R^1$ = methyl, ethyl or cyclopropyl
$R^2$ = hydrogen, methyl, ethyl, bromine, chlorine, fluorine, trifluoromethyl, methoxy, ethoxy, —$N(CH_3)_2$ or —$N(C_2H_5)_2$
$R^3$ = hydrogen, methyl, ethyl or chlorine
$R^4$ = hydrogen or methyl
$R^5$ = hydrogen
$R^6$ and $R^7$ = hydrogen, methyl or ethyl, $R^6$ and $R^7$ being identical or different

TABLE 1

| | |
|---|---|
| $R^1$ | = methyl, ethyl or cyclopropyl |
| $R^2$ | = hydrogen, methyl, ethyl, bromine, chlorine, fluorine, trifluoromethyl, methoxy, ethoxy, —$N(CH_3)_2$ or —$N(C_2H_5)_2$ |
| $R^3$ | = hydrogen, methyl, ethyl or chlorine |
| $R^4$ | = hydrogen or methyl |
| $R^5$ | = hydrogen |
| $R^6$ and $R^7$ | = hydrogen, methyl or ethyl, $R^6$ and $R^7$ being identical or different |
| Y | = bromine, chlorine or methyl in the 2-, 3- or 4-position relative to the thiazole ring and particularly preferred compounds are those compounds of the formula I in which the substituents have the meanings given below in Table 2: |

Y = bromine, chlorine or methyl in the 2-, 3- or 4-position relative to the thiazole ring
and particularly preferred compounds are those compounds of the formula I in which the substituents have the meanings given below in Table 2:

TABLE 2

| | |
|---|---|
| $R^1$ | = methyl or ethyl |
| $R^2$ | = hydrogen, methyl, chlorine, methoxy, fluorine or trifluoromethyl |
| $R^3$ | = hydrogen or methyl |
| $R^4$ | = hydrogen |
| $R^5$ | = hydrogen |
| $R^6$ and $R^7$ | = methyl or ethyl |
| Y | = chlorine in the 2-, 3- or 4-position relative to the thiazole ring |

In addition to the thiazoline derivatives described in the illustrative examples, the compounds of the general formulae I and IV which are listed in Table 3 which follows, and also their acid addition products, can also be obtained according to the invention:

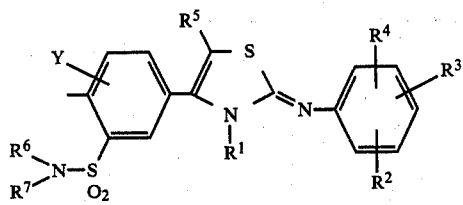

(I)

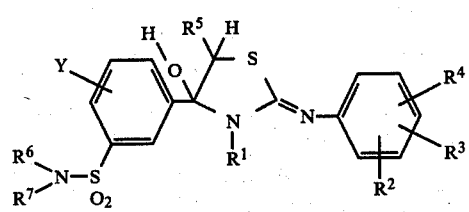

(IV)

| Serial No. | R¹ | R² | R³ | R⁴ | R⁵ | R⁶ | R⁷ | Y |
|---|---|---|---|---|---|---|---|---|
| 1 | c-Prop | H | H | H | H | H | H | 4-Cl |
| 2 | i-Prop | H | H | H | H | H | H | 4-Cl |
| 3 | Me | 2-Me | 6-Me | H | H | H | H | 4-Cl |
| 4 | Me | 3-Me | 5-Me | H | H | H | H | 4-Cl |
| 5 | Me | 2-Me | 4-Me | 6-Me | H | H | H | 4-Cl |
| 6 | Et | 2-Me | 4-Me | H | H | H | H | 4-Cl |
| 7 | Me | 2-Et | 4-Et | H | H | H | H | 4-Cl |
| 8 | Me | 2-Me | 6-Cl | H | H | H | H | 4-Cl |
| 9 | Me | H | H | H | Et | H | H | 4-Cl |
| 10 | Me | 2-Br | H | H | H | H | H | 4-Cl |
| 11 | Me | 2-Br | H | H | Et | H | H | 4-Cl |
| 12 | Me | 4-Br | H | H | H | H | H | 4-Cl |
| 13 | Me | 2-Me | H | H | Me | H | H | 4-Cl |
| 14 | Me | 2-Me | H | H | Et | H | H | 4-Cl |
| 15 | Me | 2-Me | 4-Me | H | Me | H | H | 4-Cl |
| 16 | Et | 2-Me | 4-Me | H | Me | H | H | 4-Cl |
| 17 | c-Prop | 2-Me | 4-Me | H | H | H | H | 4-Cl |
| 18 | Et | 2-Cl | H | H | H | H | H | 4-Cl |
| 19 | Me | 2-CF₃ | H | H | H | H | H | 4-Cl |
| 20 | Et | 2-CF₃ | H | H | H | H | H | 4-Cl |
| 21 | Et | 2-Me | H | H | H | H | Me | 4-Cl |
| 22 | Me | 2-Me | 4-Me | H | H | H | Me | 4-Cl |
| 23 | Me | 2-Et | 4-Et | H | H | H | Et | 4-Cl |
| 24 | Me | 3-CF₃ | H | H | H | H | Me | 4-Cl |
| 25 | Me | 4-F | H | H | H | H | Et | 4-Cl |
| 26 | Me | 4-Br | H | H | H | H | Me | 4-Cl |
| 27 | c-Prop | H | H | H | H | H | Me | 4-Cl |
| 28 | c-Prop | 2-Me | H | H | H | H | Me | 4-Cl |
| 29 | Me | 2-Br | H | H | H | H | Me | 4-Cl |
| 30 | Me | 2-Me | 4-Me | 6-Me | H | H | Me | 4-Cl |
| 31 | Me | 2-Me | H | H | H | Me | Me | 4-Cl |
| 32 | Me | 2-Cl | H | H | H | H | But | 4-Cl |
| 33 | Me | 2-Me | 4-Me | H | H | H | c-Prop | 4-Cl |
| 34 | Me | 2-Me | 3-Me | H | H | H | c-Prop | 4-Cl |
| 35 | Me | 4-F | H | H | H | H | c-Prop | 4-Cl |
| 36 | Et | 2-Me | 4-Me | H | H | H | c-Hex | 4-Cl |
| 37 | Et | 2-Cl | H | H | H | H | c-Hex | 4-Cl |
| 38 | c-Prop | H | H | H | H | H | c-Hex | 4-Cl |
| 39 | Me | 2-Cl | H | H | H | H | i-Prop | 4-Cl |
| 40 | Me | 2-Me | 5-Me | H | H | H | i-Prop | 4-Cl |
| 41 | Et | 2-Me | H | H | H | H | sec.But | 4-Cl |
| 42 | Me | 2-Cl | H | H | H | H | sec.But | 4-Cl |
| 43 | Me | 2-Me | 4-Me | H | H | H | i-But | 4-Cl |
| 44 | Me | 2-Me | 4-Me | 6-Me | H | H | Et | 4-Cl |
| 45 | Me | 4-F | H | H | H | H | Hex | 4-Cl |
| 46 | Me | H | H | H | Me | Me | Me | 4-Cl |
| 47 | Et | H | H | H | Et | Me | Me | 4-Cl |
| 48 | Me | 2-Me | H | H | Et | Me | Me | 4-Cl |
| 49 | Me | 2-Me | 4-Me | H | Me | Me | Me | 4-Cl |
| 50 | Me | 2-Cl | H | H | Et | Me | Me | 4-Cl |
| 51 | Me | 3-CF₃ | H | H | Me | Me | Me | 4-Cl |
| 52 | Me | 2-Cl | 4-Me | H | Me | Me | Me | 4-Cl |
| 53 | Me | 4-Prop | H | H | H | Me | Me | 4-Cl |
| 54 | Me | 4-But | H | H | H | Me | Me | 4-Cl |
| 55 | Me | 3-Et | H | H | H | Me | Me | 4-Cl |
| 56 | Me | 3-Prop | H | H | H | Me | Me | 4-Cl |
| 57 | Me | 3-But | H | H | H | Me | Me | 4-Cl |
| 58 | Me | 2-Et | 4-Et | H | H | Me | Me | 4-Cl |
| 59 | Me | 2-Me | 5-Me | H | H | Me | Me | 4-Cl |
| 60 | Me | 2-Me | 6-Me | H | H | Me | Me | 4-Cl |
| 61 | Me | 2-Me | 5-Et | H | H | Me | Me | 4-Cl |
| 62 | Me | 2-Me | 5-Prop | H | H | Me | Me | 4-Cl |
| 63 | Me | 2-Me | 5-i-But | H | H | Me | Me | 4-Cl |
| 64 | Me | 2-Et | 5-Et | H | H | Me | Me | 4-Cl |
| 65 | Me | 2-Me | 5-But | H | H | Me | Me | 4-Cl |
| 66 | Me | 3-Et | 4-Me | H | H | Me | Me | 4-Cl |
| 67 | Me | 3-Cl | 5-Et | H | H | Me | Me | 4-Cl |
| 68 | Me | 3-Br | 5-Et | H | H | Me | Me | 4-Cl |
| 69 | Me | 3-Et | 4-Cl | H | H | Me | Me | 4-Cl |
| 70 | Me | 3-Et | 4-Br | H | H | Me | Me | 4-Cl |
| 71 | Me | 2-Cl | 5-Me | H | H | Me | Me | 4-Cl |
| 72 | Me | 2-Cl | 5-Et | H | H | Me | Me | 4-Cl |
| 73 | Me | 2-Cl | 5-Prop | H | H | Me | Me | 4-Cl |
| 74 | Me | 2-Cl | 5-But | H | H | Me | Me | 4-Cl |
| 75 | Me | 2-Cl | 5-i-But | H | H | Me | Me | 4-Cl |
| 76 | Me | 2-Br | 5-Et | H | H | Me | Me | 4-Cl |
| 77 | Me | 2-Br | 5-Prop | H | H | Me | Me | 4-Cl |
| 78 | Me | 2-MeO | 5-Me | H | H | Me | Me | 4-Cl |
| 79 | Me | 2-MeO | 5-Et | H | H | Me | Me | 4-Cl |
| 80 | Me | 2-MeO | 5-i-But | H | H | Me | Me | 4-Cl |
| 81 | Me | 2-EtO | 5-Me | H | H | Me | Me | 4-Cl |
| 82 | Me | 2-EtO | 5-Et | H | H | Me | Me | 4-Cl |
| 83 | Me | 2-PropO | 4-Et | H | H | Me | Me | 4-Cl |
| 84 | Me | 2-PropO | 5-Et | H | H | Me | Me | 4-Cl |
| 85 | Me | 3-Me | 4-OMe | H | H | Me | Me | 4-Cl |
| 86 | Me | 3-Me | 4-OEt | H | H | Me | Me | 4-Cl |
| 87 | Me | 3-Et | 4-OMe | H | H | Me | Me | 4-Cl |
| 88 | Me | 2-Me | 4-Me | 6-Me | H | Me | Me | 4-Cl |
| 89 | Me | 2-Me | 4-Me | 5-Et | H | Me | Me | 4-Cl |
| 90 | Me | 2-Cl | 4-Cl | 5-Et | H | Me | Me | 4-Cl |
| 91 | Me | 2-Me | 3-Me | 5-Et | H | Me | Me | 4-Cl |
| 92 | Me | 2-MeO | 3-Me | 5-Me | H | Me | Me | 4-Cl |
| 93 | Me | 2-MeO | 3-Me | 5-Et | H | Me | Me | 4-Cl |
| 94 | Me | 2-MeO | 3-Cl | 5-Et | H | Me | Me | 4-Cl |
| 95 | Me | 2-MeO | 3-MeO | 5-Me | H | Me | Me | 4-Cl |
| 96 | Me | 2-MeO | 3-MeO | 5-Et | H | Me | Me | 4-Cl |
| 97 | Me | 2-MeO | 4-MeO | 5-Et | H | Me | Me | 4-Cl |
| 98 | Me | 2-Me | 4-Me | 5-Me | H | Me | Me | 4-Cl |
| 99 | Et | 2-Me | 4-Me | H | H | Me | Me | 4-Cl |
| 100 | Et | 2-Me | 4-Cl | H | H | Me | Me | 4-Cl |
| 101 | Et | 3-CF₃ | H | H | H | Me | Me | 4-Cl |
| 102 | Et | 4-F | H | H | H | Me | Me | 4-Cl |
| 103 | Et | 2-Et | 4-Et | H | H | Me | Me | 4-Cl |
| 104 | Et | 2-CF₃ | H | H | H | Me | Me | 4-Cl |
| 105 | Et | 4-NEt₂ | H | H | H | Me | Me | 4-Cl |
| 106 | Me | 2-CF₃ | H | H | H | Me | Me | 4-Cl |
| 107 | Et | 4-OMe | H | H | H | Me | Me | 4-Cl |
| 108 | c-Prop | 2-Me | H | H | H | Me | Me | 4-Cl |
| 109 | c-Prop | 2-Me | 4-Me | H | H | Me | Me | 4-Cl |
| 110 | c-Prop | 2-Cl | H | H | H | Me | Me | 4-Cl |
| 111 | c-Prop | 4-OMe | H | H | H | Me | Me | 4-Cl |
| 112 | Me | 2-Me | 4-Me | H | H | Et | Et | 4-Cl |
| 113 | Me | 2-Cl | H | H | H | Et | Et | 4-Cl |
| 114 | Me | 2-Br | H | H | H | Et | Et | 4-Cl |
| 115 | Me | 2-Me | 6-Me | H | H | Et | Et | 4-Cl |
| 116 | Me | 3-CF₃ | H | H | H | Et | Et | 4-Cl |
| 117 | Me | 4-CF₃ | H | H | H | Et | Et | 4-Cl |
| 118 | Me | 4-MeO | H | H | H | Et | Et | 4-Cl |
| 119 | Me | 4-F | H | H | H | Et | Et | 4-Cl |
| 120 | Me | 2-Me | 4-Me | H | Me | Et | Et | 4-Cl |
| 121 | Me | H | H | H | H | H | H | 4-Br |
| 122 | Me | 2-Me | H | H | H | H | H | 4-Br |
| 123 | Me | 2-Cl | H | H | H | H | H | 4-Br |
| 124 | Me | 2-Me | 4-Me | H | H | H | H | 4-Br |
| 125 | Me | 2-Me | 6-Me | H | H | H | H | 4-Br |
| 126 | Me | 4-MeO | H | H | H | H | H | 4-Br |
| 127 | Me | 4-F | H | H | H | H | H | 4-Br |
| 128 | Me | 3-CF₃ | H | H | H | H | H | 4-Br |
| 129 | Me | 2-Cl | 6-Cl | H | H | Me | Me | 4-Cl |
| 130 | Me | 2-Cl | 4-Cl | H | H | Me | Me | 4-Cl |
| 131 | Me | 2-Me | H | H | H | Me | Me | 4-Br |
| 132 | Me | 2-Cl | H | H | H | Me | Me | 4-Br |

-continued

| Serial No. | R¹ | R² | R³ | R⁴ | R⁵ | R⁶ | R⁷ | Y |
|---|---|---|---|---|---|---|---|---|
| 133 | Me | 2-Me | 4-Me | H | H | Me | Me | 4-Br |
| 134 | Me | 2-Me | 3-Me | H | H | Me | Me | 4-Br |
| 135 | Me | 2-Me | 6-Me | H | H | Et | Et | 4-Br |
| 136 | Me | 2-Cl | 6-Cl | H | H | Et | Et | 4-Br |
| 137 | Me | 2-Cl | 6-Cl | H | H | Me | Me | 4-Br |
| 138 | Me | 2-Me | 6-Me | H | H | Me | Me | 4-Br |
| 139 | Me | 4-MeO | H | H | H | Me | Me | 4-Br |
| 140 | Me | 4-F | H | H | H | Me | Me | 4-Br |
| 141 | Me | H | H | H | H | H | H | 4-F |
| 142 | Me | 2-Cl | H | H | H | H | H | 4-F |
| 143 | Et | 2-Cl | H | H | H | H | H | 4-F |
| 144 | Me | 2-Me | 4-Me | H | H | H | H | 4-F |
| 145 | Me | 2-Me | H | H | H | Me | Me | 4-F |
| 146 | Me | 2-Me | 4-Me | H | H | Me | Me | 4-F |
| 147 | Me | 2-Cl | H | H | H | Me | Me | 4-F |
| 148 | Me | 2-Br | H | H | H | Me | Me | 4-F |
| 149 | Me | 4-Cl | H | H | H | Me | Me | 4-F |
| 150 | Me | 2-Cl | 4-Cl | H | H | Me | Me | 4-F |
| 151 | Me | 4-F | H | H | H | Me | Me | 4-F |
| 152 | Me | 4-MeO | H | H | H | Me | Me | 4-F |
| 153 | Me | 2-Me | 3-Me | H | H | Me | Me | 4-F |
| 154 | Et | 3-CF₃ | H | H | H | Me | ME | 4-F |
| 155 | Et | 2-Cl | H | H | H | Me | Me | 4-F |
| 156 | Et | 2-Me | 4-Me | H | H | Me | Me | 4-F |
| 157 | Me | 2-Me | H | H | H | Et | Et | 4-F |
| 158 | Me | 2-Me | 4-Me | H | H | Et | Et | 4-F |
| 159 | Me | 2-Cl | H | H | H | Et | Et | 4-F |
| 160 | Me | 4-MeO | H | H | H | Et | Et | 4-F |
| 161 | Me | H | H | H | H | H | H | 4-H |
| 162 | Me | Cl | H | H | H | H | H | 4-H |
| 163 | Me | Br | H | H | H | H | H | 4-H |
| 164 | Me | 2-Me | 4-Me | H | H | H | H | 4-H |
| 165 | Et | Cl | H | H | H | H | H | 4-H |
| 166 | Et | H | H | H | H | H | H | 4-H |
| 167 | c-Prop | H | H | H | H | H | H | 4-H |
| 168 | Me | H | H | H | H | Me | Me | 4-H |
| 169 | Me | 2-Cl | H | H | H | Me | Me | 4-H |
| 170 | Me | 2-Br | H | H | H | Me | Me | 4-H |
| 171 | Me | 2-Me | 3-Me | H | H | Me | Me | 4-H |
| 172 | Me | 2-Me | 4-Me | H | H | Me | Me | 4-H |
| 173 | Me | 2-Me | 6-Me | H | H | Me | Me | 4-H |
| 174 | Et | 2-Me | 4-Me | H | H | Me | Me | 4-H |
| 175 | Me | 4-OMe | H | H | H | Me | Me | 4-H |
| 176 | Me | 3-CF₃ | H | H | H | Me | Me | 4-H |
| 177 | Et | 2-Me | H | H | H | Me | Me | 4-H |
| 178 | c-Prop | 2-Me | H | H | H | Me | Me | 4-H |
| 179 | Et | 2-Cl | H | H | H | Me | Me | 4-H |
| 180 | Me | 4-Cl | H | H | H | Me | Me | 4-H |
| 181 | Me | H | H | H | H | H | H | 4-Me |
| 182 | Et | H | H | H | H | H | H | 4-Me |
| 183 | Me | 2-Me | H | H | H | H | H | 4-Me |
| 184 | Me | 2-Et | H | H | H | H | H | 4-Me |
| 185 | Et | 2-Me | H | H | H | H | H | 4-Me |
| 186 | Me | 2-Cl | H | H | H | H | H | 4-Me |
| 187 | Me | 2-Br | H | H | H | H | H | 4-Me |
| 188 | Me | 2-Cl | 4-Me | H | H | H | H | 4-Me |
| 189 | Et | 2-Cl | H | H | H | H | H | 4-Me |
| 190 | Me | 4-MeO | H | H | H | H | H | 4-Me |
| 191 | Me | 4-Cl | H | H | H | H | H | 4-Me |
| 192 | Me | 4-F | H | H | H | H | H | 4-Me |
| 193 | Et | 4-F | H | H | H | H | H | 4-Me |
| 194 | Me | 3-CF₃ | H | H | H | H | H | 4-Me |
| 195 | Me | 4-CF₃ | H | H | H | H | H | 4-Me |
| 196 | Me | 2-Me | 4-Me | H | H | H | H | 4-Me |
| 197 | Et | 2-Me | 4-Me | H | H | H | H | 4-Me |
| 198 | Me | 2-Me | 3-Me | H | H | H | H | 4-Me |
| 199 | Me | 2-Me | 6-Me | H | H | H | H | 4-Me |
| 200 | Me | 2-Cl | 6-Cl | H | H | H | H | 4-Me |
| 201 | Me | H | H | H | H | H | Me | 4-Me |
| 202 | Me | 2-Me | H | H | H | H | Me | 4-Me |
| 203 | Me | 2-Me | 4-Me | H | H | H | Me | 4-Me |
| 204 | Me | 2-Cl | H | H | H | H | Me | 4-Me |
| 205 | Me | H | H | H | H | Me | Me | 4-Me |
| 206 | Et | H | H | H | H | Me | Me | 4-Me |
| 207 | c-Prop | H | H | H | H | Me | Me | 4-Me |
| 208 | Me | 2-Me | H | H | H | Me | Me | 4-Me |
| 209 | Me | 2-Et | H | H | H | Me | Me | 4-Me |
| 210 | Et | 2-Me | H | H | H | Me | Me | 4-Me |
| 211 | Me | 2-Cl | H | H | H | Me | Me | 4-Me |
| 212 | Me | 2-Br | H | H | H | Me | Me | 4-Me |
| 213 | Et | 2-Cl | H | H | H | Me | Me | 4-Me |
| 214 | c-Prop | 2-Cl | H | H | H | Me | Me | 4-Me |
| 215 | Me | 4-MeO | H | H | H | Me | Me | 4-Me |
| 216 | Me | 4-Cl | H | H | H | Me | Me | 4-Me |
| 217 | Me | 4-F | H | H | H | Me | Me | 4-Me |
| 218 | Et | 4-F | H | H | H | Me | Me | 4-Me |
| 219 | Me | 3-CF₃ | H | H | H | Me | Me | 4-Me |
| 220 | Me | 4-CF₃ | H | H | H | Me | Me | 4-Me |
| 221 | Me | 2-Me | 4-Me | H | H | Me | Me | 4-Me |
| 222 | Me | 2-Me | 4-Me | 6-Me | H | Me | Me | 4-Me |
| 223 | Et | 2-Me | 4-Me | H | H | Me | Me | 4-Me |
| 224 | Me | 2-Me | 6-Me | H | H | Me | Me | 4-Me |
| 225 | Me | 2-Me | 3-Me | H | H | Me | Me | 4-Me |
| 226 | Me | 2-Cl | 6-Cl | H | H | Me | Me | 4-Me |
| 227 | c-Prop | 2-Me | 4-Me | H | H | Me | Me | 4-Me |
| 228 | Et | 2-Br | H | H | H | Me | Me | 4-Me |
| 229 | Me | 2-Me | H | H | H | Et | Et | 4-Me |
| 230 | Me | 2-Me | 4-Me | H | H | Et | Et | 4-Me |
| 231 | Me | H | H | H | H | Et | Et | 4-Me |
| 232 | Me | 2-Cl | H | H | H | Et | Et | 4-Me |
| 233 | Me | 4-F | H | H | H | Et | Et | 4-Me |
| 234 | Me | 4-CF₃ | H | H | H | Et | Et | 4-Me |
| 235 | Me | H | H | H | H | H | H | 4-i-Prop |
| 236 | Me | H | H | H | H | Me | Me | 4-i-Prop |
| 237 | Me | 2-Me | 4-Me | H | H | Me | Me | 4-i-Prop |
| 238 | Me | 2-Cl | H | H | H | Me | Me | 4-i-Prop |
| 239 | Et | 2-Me | H | H | H | Me | Me | 4-i-Prop |
| 240 | Me | 2-Me | 6-Me | H | H | Me | Me | 4-i-Prop |
| 241 | Me | 2-Br | H | H | H | Me | Me | 2-Cl |
| 242 | Me | 3-Cl | H | H | H | Me | Me | 2-Cl |
| 243 | Me | 4-Cl | H | H | H | Me | Me | 2-Cl |
| 244 | Me | 3-CF₃ | H | H | H | Me | Me | 2-Cl |
| 245 | Me | 2-F | H | H | H | Me | Me | 2-Cl |
| 246 | Me | 2-Me | 4-Me | H | H | Me | Me | 2-Cl |
| 247 | Me | 2-Cl | 4-Me | H | H | Me | Me | 2-Cl |
| 248 | Me | 4-MeO | H | H | H | Me | Me | 2-Cl |
| 249 | Me | 2-Me | 4-MeO | H | H | Me | Me | 2-Cl |
| 250 | Me | 2-Cl | 4-MeO | H | H | Me | Me | 2-Cl |
| 251 | Me | 3-F | H | H | H | Me | Me | 2-Cl |
| 252 | Me | 4-F | H | H | H | Me | Me | 2-Cl |
| 253 | Me | 4-Br | H | H | H | Me | Me | 2-Cl |
| 254 | Me | H | H | H | H | Et | Et | 2-Cl |
| 255 | Et | H | H | H | H | Et | Et | 2-Cl |
| 256 | c-Prop | H | H | H | H | Et | Et | 2-Cl |
| 257 | Prop | H | H | H | H | Et | Et | 2-Cl |
| 258 | Me | 2-Cl | H | H | H | Et | Et | 2-Cl |
| 259 | Me | 4-Cl | H | H | H | Et | Et | 2-Cl |
| 260 | Me | 2-Me | H | H | H | Et | Et | 2-Cl |
| 261 | Me | 2-Me | 4-Me | H | H | Et | Et | 2-Cl |
| 262 | Me | 3-CF₃ | H | H | H | Et | Et | 2-Cl |
| 263 | Me | 4-OMe | H | H | H | Et | Et | 2-Cl |
| 264 | Me | 2-Br | H | H | H | Et | Et | 2-Cl |
| 265 | Me | H | H | H | H | Me | Prop | 2-Cl |
| 266 | Me | 2-Cl | H | H | H | Me | Prop | 2-Cl |
| 267 | Me | 4-MeO | H | H | H | Me | Prop | 2-Cl |
| 268 | Me | 4-Cl | H | H | H | Me | Prop | 2-Cl |
| 269 | Me | 2-Me | 4-Me | H | H | Me | Prop | 2-Cl |
| 270 | Me | 2-Cl | H | H | H | Me | Me | 3-Cl |
| 271 | Me | 4-MeO | H | H | H | Me | Me | 3-Cl |
| 272 | Me | 4-Cl | H | H | H | Me | Me | 3-Cl |
| 273 | Me | 2-Me | 4-Me | H | H | H | Me | 3-Cl |
| 274 | Me | H | H | H | H | H | Me | 3-Cl |
| 275 | Me | H | H | H | H | Me | Prop | 3-Cl |
| 276 | Me | 2-Cl | H | H | H | Me | Prop | 3-Cl |
| 277 | Me | H | H | H | H | Et | Et | 3-Cl |
| 278 | Et | H | H | H | H | Et | Et | 3-Cl |
| 279 | Me | 2-Cl | H | H | H | Et | Et | 3-Cl |
| 280 | Me | 2-Me | 4-Me | H | H | Et | Et | 3-Cl |
| 281 | Me | 4-MeO | H | H | H | Et | Et | 3-Cl |

The compounds, according to the invention, of the formula I are valuable medicaments and are distinguished by a very advantageous effect on the serum lipoproteins. They can therefore be used as medicaments, especially for influencing the serum lipoproteins. The invention therefore also relates to pharmaceutical preparations based on the compounds of the formula I and their pharmacologically acceptable salts, and to the use as medicaments.

It is reported in the literature that 4-phenyl-2,3-dihydrothiazoline derivatives have an anorectic, central nervous system-stimulating and diuretic action, the derivatives under discussion being compounds which do not have a sulfonamide substituent in the phenyl part and in which the 2-imino group is not substituted by aryl (compare U.S. Pat. No. 3,671,533 and German Offenlegungsschrift 1,938,674). 3-Alkyl-4-phenyl-2-phenylimino-4-thiazolines in which the phenyl radical present in the 4-position does not carry a sulfonamide group have also been described (compare Univ. Kansas Sci. Bull. 24, 45–49 (1936)). 4-(3-Sulfamoyl-phenyl)-3-alkyl-2-imino-4-thiazolines and -thiazolidines with different substituents are likewise mentioned in the literature, specifically in particular as diuretic agents (compare "Diuretic Agents", E. J. Cragoe, Jr., Editor: ACS-Symposium Series 83, page 24, Washington D.C., 1978).

It was, then, surprising that the compounds, according to the invention, of the formula I display a very powerful and advantageous effect on the serum lipoproteins, whilst the thiazoline derivatives described in the abovementioned literature give rise to no effects or only to slight effects which are distinctly inferior from the qualitative and quantitative standpoint.

It is generally recognized that hyperlipoproteinaemia constitutes a considerable risk factor for the development of arteriosclerotic vascular changes, especially in coronary heart disease. The lowering of elevated serum lipoprotein levels is therefore of exceptional importance for the prophylaxis and the regression of arteriosclerotic changes. However, it is very specific categories of serum lipoproteins which are concerned here, since the low density lipoproteins (LDL) and very low density lipoproteins (VLDL) constitute an atherogenic risk factor, whilst the high density lipoproteins (HDL) constitute a protective function against coronary heart disease. Accordingly, hypolipidaemic agents should lower the levels of VLDL-cholesterol and LDL-cholesterol in the serum, but as far as possible should have no effect on, or should even increase, the HDL-cholesterol concentration. The compounds, according to the invention, which are mentioned here have valuable therapeutic properties. Thus, they lower, in particular, the concentration of LDL and VLDL, whilst the HDL fraction is either reduced to a substantially lesser extent or is even increased. They therefore represent a considerable advance, compared with the comparison compound clofibrate, as can be seen from the test described below. They can therefore be used for the prophylaxis and regression of arteriosclerotic changes, in that they eliminate a causal risk factor. This risk factor includes not only primary hyperlipoproteinaemia, but also certain secondary hyperlipidaemias, such as arise, for example, in diabetes. The relative liver weight is not changed by the compounds I, whilst clofibrate, which is used as a hypolipidaemic standard, results in a substantial increase in the relative liver weight.

The effect of the compounds listed in the table which follows on the serum lipoproteins was studied on male Wistar rats, which were treated for 7 days, per probang, with the compounds listed, as suspensions in polyethylene glycol 400. In addition, a control group which received only the solvent polyethylene glycol 400 was also included in the study, and in most of the tests one group of rats to which the standard hypolipidaemic agent clofibrate was administered was also included. As a rule, 10 animals were employed per group and, at the end of the treatment, blood was taken from the orbital plexus of these rats, after they had been subjected to mild ether narcosis, and the serum obtained therefrom was pooled for separation of the categories of lipoproteins in the preparative ultra-centrifuge by the methods currently in use. The serum lipoproteins were separated in the ultracentrifuge into the following density categories: VLDL 1.006; LDL 1.006 to 1.04; HDL 1.04 to 1.21.

The cholesterol content of the lipoprotein fractions isolated in the ultracentrifuge was determined completely enzymatically by the CHOD-PAP method by means of the Boehringer-Mannheim test combination and the values obtained were converted to $\mu g/ml$ of serum. The change in the lipoprotein cholesterol in the treated group compared with that in a control group included in the study under the same conditions is shown in the table given. As can be seen from the table, clofibrate effects an approximately equal lowering of the LDL fraction and a severe lowering of the HDL fraction, whilst the novel compounds exert a powerful selectively lowering action on the atherogenic lipoprotein fractions (VLDL and LDL) and leave the protecting HDL fraction essentially unaffected, or even increase this fraction.

TABLE

Change in the serum lipoprotein level in rats after a 7 day period of peroral treatment with the compounds

| Compound according to | Dose mg/kg per day | % change in the cholesterol (compared with the control group) | | | |
|---|---|---|---|---|---|
| | | in the serum | in the serum lipoprotein fractions | | |
| | | | VLDL | LDL | HDL |
| Example 2 | 100 | −17 | −77 | −56 | −3 |
| | 30 | −8 | −57 | −43 | −4 |
| | 10 | −5 | −26 | −38 | −2 |
| | 3 | +2 | +23 | −39 | +9 |
| | 1 | 0 | | −39 | +13 |
| Example 13 | 30 | −12 | −18 | −32 | 0 |
| | 10 | −12 | 0 | −41 | −13 |
| | 3 | −14 | −15 | −31 | −3 |
| | 1 | +7 | −36 | −14 | +13 |
| Example 19 | 10 | −8 | −41 | −53 | +3 |
| | 3 | −11 | −85 | −41 | −2 |
| | 1 | −8 | −57 | −12 | −2 |
| Example 353 | 3 | −6 | −33 | −61 | +4 |
| | 1 | +8 | −10 | −30 | +4 |
| | 0.3 | −9 | −14 | −25 | −5 |
| | 0.1 | +7 | −17 | −23 | +2 |
| Example 354 | 30 | −15 | −50 | −60 | −9 |
| | 3 | −18 | −23 | −66 | −4 |
| | 1 | +3 | | −43 | +9 |
| clofibrate | 100 | −47 | −30 | −33 | −38 |

A therapeutic formulation of the compounds of the formula I can be, in particular, in the form of tablets, sugar-coated tablets, capsules, suppositories or syrups. The novel compounds can be used either on their own or as a mixture with pharmacologically acceptable excipients. An oral administration form is preferred. For this purpose, the active compounds are preferably mixed with substances which are in themselves known and converted, by methods which are in themselves known, to suitable administration forms, such as tablets, gelatin capsules, aqueous or oily suspensions or aqueous or oily solutions. Inert excipients which can be used are, for example, magnesium carbonate, lactose or maize starch, with the addition of other substances, such as, for example, magnesium stearate. The formulation can be prepared in the form of either dry granules or moist granules. Oily excipients or solvents which can be used are, in particular, vegetable and animal oils, such as, for example, sunflower oil or codliver oil. The daily dose can be about 50 mg to 5 g. One dosage unit preferably contains 250 to 500 mg.

For the treatment of lipid metabolism disorders, the formulations can also contain, in addition to the conventional fillers and excipients, an antihypertensive agent, such as, for example, a saluretic agent, reserpine, hydralazine, guanethidine, α-methyl-dopa, clonidine or a β-sympathicolytic agent, or an agent having an antihyperuricaemic action, an oral antidiabetic agent, an agent for the treatment of geriatric symptoms or an agent which improves the circulation.

Compared with the compounds, according to the invention, of the formula I, the pure precursors, according to the invention, of the general formula IV have a distinctly weaker effect on the serum lipoproteins—if they have any effect at all—but, like structurally related thiazolidine derivatives (compare German Offenlegungsschrift 2,436,263), they possess a salidiuretic activity, which is very good in some cases.

The melting points and decomposition temperatures given in the examples which follow are not corrected.

EXAMPLE 1

4-(4-Chloro-3-dimethylsulfamoylphenyl)-3-methyl-2-phenylimino-4-thiazoline hydrobromide (a) 6.8 g (0.02 mole) of 2-bromo-4'-chloro-3'-dimethylsulfamoyl-acetophenone and 3.3 g (0.02 mole) of 1-methyl-3-phenyl-thiourea in 100 ml of ethanol are heated to the boil in the course of 1 hour. 50 ml of glacial acetic acid are added and the mixture is heated at the boil for a further 2 to 3 hours. After distilling off the solvent under a waterpump vacuum, diisopropyl ether, ethyl acetate or diethyl ether is added to the residue and the product is filtered off. Colorless crystals; melting point 258°–260° C. (with decomposition).

(b) 10.1 g (0.02 mole) of 4-(4-chloro-3-dimethylsulfamoylphenyl)-3-methyl-2-phenyliminothiazolidin-4-ol hydrobromide in 80 ml of glacial acetic acid are heated to the boil over a period of 20 minutes. After cooling, crystallization is brought to completion by adding about 150 ml of diisopropyl ether, the mixture is stirred for a further one hour at room temperature and the product is filtered off. Colorless crystals; melting point 258°–260° C. (with decomposition).

EXAMPLE 2

4-(4-Chloro-3-dimethylsulfamoylphenyl)-3-methyl-2-phenylimino-4-thiazoline (a) 10 ml of triethylamine are added to a suspension of 9.8 g (0.02 mole) of 4-(4-chloro-3-dimethylsulfamoylphenyl)-3-methyl-2-phenylimino-4-thiazoline hydrobromide in 200 ml of methanol. The mixture is stirred for 3 hours at about 20° to 30° C. and the solvent is removed under reduced pressure. The residue is stirred in 100 ml of water for 2 hours and the crystals are filtered off. Melting point 179°–181° C.

(b) 8.52 g (0.02 mole) of 4-(4-chloro-3-dimethylsulfamoylphenyl)-3-methyl-2-phenyliminothiazolidin-4-ol in 100 ml of glacial acetic acid are heated at the boil for 3 hours, the solvent is distilled off and the residue is made to crystallize using water. Melting point 180° C.

EXAMPLE 3

4-(4-Chloro-3-dimethylsulfamoylphenyl)-3-methyl-2-phenylimino-4-thiazoline hydrochloride (a) Obtained analogously to Example 1 (a) from 2,4'-dichloro-3'-dimethylsulfamoyl-acetophenone and 1-methyl-3-phenylthiourea. Colorless crystals; melting point 228° C. (with decomposition).

(b) 8.52 g (0.02 mole) of 4-(4-chloro-3-dimethylsulfamoylphenyl)-3-methyl-2-phenyliminothiazolidin-4-ol in 125 ml of methanol are rendered strongly acid with an ethereal solution of hydrochloric acid and the solvent is distilled off. The residue is heated in 100 ml of glacial acetic acid at the boil for 1 hour, the solvent is distilled off and the residue is made to crystallize using ethyl acetate. Colorless crystals; melting point 228°–231° C. (with decomposition) (from ethanol).

(c) 8.9 g (0.02 mole) of 4-(4-chloro-3-dimethylsulfamoylphenyl)-3-methyl-2-phenylimino-4-thiazoline in 150 ml of methanol are acidified with a saturated ethereal solution of hydrogen chloride, the solvent is distilled off and the residue is recrystallized from ethanol. Melting point 229°–233° C. (with decomposition).

EXAMPLE 4

4-(4-Chloro-3-dimethylsulfamoylphenyl)-3-methyl-2-phenylimino-4-thiazoline methanesulfonate Obtained by a procedure analogous to that indicated in Example 3 (c), from 4-(4-chloro-3-dimethylsulfamoylphenyl)-3-methyl-2-phenylimino-4-thiazoline and 0.02 mole of methanesulfonic acid. Colorless crystals; melting point 198°–199° C.

EXAMPLE 5

4-(4-Chloro-3-dimethylsulfamoylphenyl)-3-methyl-2-phenylimino-4-thiazoline p-toluenesulfonate Obtained by a procedure analogous to that indicated in Example 3(c), from 4-(4-chloro-3-dimethylsulfamoylphenyl)-3-methyl-2-phenylimino-4-thiazoline and 0.02 mole of p-toluenesulfonic acid. Colorless crystals; melting point 196° C.

EXAMPLE 6

4-(4-Chloro-3-dimethylsulfamoylphenyl)-3-methyl-2-(2-methylphenylimino)-4-thiazoline hydrobromide Obtained by a procedure analogous to that indicated in Example 1 (b), from 4-(4-chloro-3-dimethylsulfamoylphenyl)-3-methyl-2-(2-methylphenylimino)-thiazolidin-4-ol hydrobromide, and the crystals which precipitate as a sparingly double compound from glacial acetic acid are filtered off at room temperature. Colorless crystals; melting point 256° C.

EXAMPLE 7

4-(4-Chloro-3-dimethylsulfamoylphenyl)-3-methyl-2-(2-methylphenylimino)-4-thiazoline Obtained by a procedure analogous to that indicated in Example 2 (a), from 4-(4-chloro-3-dimethylsulfamoylphenyl)-3-methyl-2-(2-methylphenylimino)-4-thiazoline hydrobromide with triethylamine in methanol. Colorless crystals from methanol/ethyl acetate; melting point 158°–162° C.

EXAMPLE 8

4-(4-Chloro-3-dimethylsulfamoylphenyl)-2-(4-fluorophenylimino)-3-methyl-4-thiazoline hydrobromide (a) Obtained by a procedure analogous to that indicated in Example 1 (a), from 2-bromo-4'-chloro-3'-dimethylsulfamoyl-acetophenone and 1-(4-fluorophenyl)-3-methylthiourea. Colorless crystals; melting point 251°–253° C. (with decomposition) or (b) Obtained by a procedure analogous to that indicated in Example 1 (b), from 4-(4-chloro-3-dimethylsulfamoylphenyl)-2-(4-fluorophenylimino)-thiazolidin-4-ol hydrobromide. Colorless crystals; melting point 252° C.

EXAMPLE 9

4-(4-Chloro-3-dimethylsulfamoylphenyl)-2-(4-fluorophenylimino)-3-methyl-4-thiazoline Obtained by a procedure analogous to that indicated in Example 2 (a), from 4-(4-chloro-3-dimethylsulfamoylphenyl)-2-(4-fluorophenyl-imino)-3-methyl-4-thiazoline hydrobromide. Colorless to pale yellow crystals; melting point 144°–145° C.

EXAMPLE 10

2-(4-Diethylaminophenyl-imino)-4-(4-chloro-3-dimethylsulfamoylphenyl)-3-methyl-4-thiazoline hydrobromide Obtained by a procedure analogous to that indicated in Example 1 (b), from 2-(4-diethylaminophenyl-imino)-4-(4-chloro-3-dimethylsulfamoylphenyl)-3-methylthiazolidin-4-ol hydrobromide. After heating in glacial acetic acid, the solvent is distilled off until the volume is 30 ml, and the desired product is precipitated with 150 ml of diisopropyl ether. Colorless crystals; melting point 257° C. (with decomposition).

EXAMPLE 11

2-(4-Diethylaminophenyl-imino)-4-(4-chloro-3-dimethylsulfamoylphenyl)-3-methyl-4-thiazoline Obtained by a procedure analogous to that indicated in Example 2 (a), from 2-(4-diethylaminophenyl-imino)-4-(4-chloro-3-dimethylsulfamoylphenyl)-3-methyl-4-thiazoline hydrobromide and triethylamine in methanol at room temperature. Melting point 184°–185° C.

EXAMPLE 12

4-(4-Chloro-3-dimethylsulfamoylphenyl)-2-(2-chlorophenyl-imino)-3-methyl-4-thiazoline hydrobromide Obtained (a) by a procedure analogous to that indicated in Example 1 (a), from 2-bromo-4'-chloro-3'-dimethylsulfamoylacetophenone and 1-(2-chlorophenyl)-3-methylthiourea. After heating under reflux, the reaction mixture is cooled, three times the volume of diisopropyl ether is added, the resulting mixture is stirred for 2 hours at room temperature and the crystals are filtered off. Melting point 246°–248° C.

(b) By a procedure analogous to that indicated in Example 1 (b), from 4-(4-chloro-3-dimethylsulfamoylphenyl)-2-(2-chlorophenyl-imino)-3-methylthiazolidin-4-ol hydrobromide. Colorless crystals: melting point 248° C.

EXAMPLE 13

4-(4-Chloro-3-dimethylsulfamoylphenyl)-2-(2-chlorophenylimino)-3-methyl-4-thiazoline (a) Obtained by a procedure analogous to that indicated in Example 2 (a), from the hydrobromide, of the title compound and triethylamine. Colorless crystals; melting point 152°–154° (from ethanol).

(b) Obtained by a procedure analogous to that indicated in Example 2 (b), by boiling 4-(4-chloro-3-dimethylsulfamoylphenyl)-2-(2-chlorophenyl-imino)-3-methylthiazolidin-4-ol in glacial acetic acid for 20 minutes and then subjecting to analogous working up. Melting point 155°–157° C. (from ethanol).

(c) 10.8 g of 4-(4-chloro-3-dimethylsulfamoylphenyl)-2-(2-chlorophenyl-imino)-3-methylthiazolidin-4-ol hydrobromide are heated at the boil in a mixture of 100 ml of methanol and 10 ml of triethylamine for 30 minutes and the reaction mixture is then poured into an equal volume of water. The resulting mixture is stirred for about 2 hours at room temperature and the crystals are filtered off and recrystallized from ethanol. Melting point 153°–156° C.

EXAMPLE 14

4-(4-Chloro-3-dimethylsulfamoylphenyl)-2-(4-methoxyphenyl-imino)-3-methyl-4-thiazoline hydrobromide Obtained by a procedure analogous to that indicated in Example 1 (b), from 4-(4-chloro-3-dimethylsulfamoylphenyl)-2-(4-methoxyphenyl-imino)-3-methylthiazolidin-4-ol hydrobromide. After distilling off the glacial acetic acid, the residue is several times boiled with acetone and the crystals are filtered off. Melting point 240°–241° C. (with decomposition).

EXAMPLE 15

4-(4-Chloro-3-dimethylsulfamoylphenyl)-2-(4-methoxyphenyl-imino)-3-methyl-4-thiazoline Obtained by a procedure analogous to that indicated in Example 2 (a), from the hydrobromide of the title compound (Example 14) and triethylamine in ethanol. Colorless crystals; melting point 198°–199° C.

EXAMPLE 16

4-(4-Chloro-3-dimethylsulfamoylphenyl)-3-methyl-2-(4-trifluoromethylphenyl-imino)-4-thiazoline hydrobromide Obtained by a procedure analogous to that indicated in Example 1 (b), from 4-(4-chloro-3-dimethylsulfamoylphenyl)-3-methyl-2-(4-trifluoromethylphenylimino)-thiazolidin-4-ol hydrobromide. Colorless crystals; melting point 228° C.

EXAMPLE 17

4-(4-Chloro-3-dimethylsulfamoylphenyl)-3-methyl-2-(4-trifluoromethylphenyl-imino)-4-thiazoline Obtained by a procedure analogous to that indicated in Example 2 (a), from the hydrobromide of the title compound of Example 16 and triethylamine. Melting point 147°–151° C.

EXAMPLE 18

4-(4-Chloro-3-dimethylsulfamoylphenyl)-3-methyl-2-(2,4-dimethylphenyl-imino)-4-thiazoline hydrobromide (a) Obtained by a procedure analogous to that indicated in Example 1 (a), from 2-bromo-4'-chloro-3'-dimethylsulfamoylacetophenone and 1-(2,4-dimethylphenyl)-3-methylthiourea. After driving off the solvent, the residue is heated at the boil in 100 ml of acetone, the mixture is cooled to room temperature and the crystals are filtered off. Melting point 262°–264° C. (with decomposition).

(b) Obtained by a procedure analogous to that indicated in Example 1 (b), from 4-(4-chloro-3-dimethylsulfamoylphenyl)-3-methyl-2-(2,4-dimethylphenyl-imino)-thiazolidin-4-ol hydrobromide. Colorless crystals; melting point 264° C. (from glacial acetic acid).

EXAMPLE 19

4-(4-Chloro-3-dimethylsulfamoylphenyl)-3-methyl-2-(2,4-dimethylphenyl-imino)-4-thiazoline Obtained by a procedure analogous to that indicated in Example 2 (a), from 4-(4-chloro-3-dimethylsulfamoylphenyl)-3-methyl-2-(2,4-dimethylphenyl-imino)-4-thiazoline hydrobromide. Colorless crystals; melting point 152°–154° C.

EXAMPLE 20

2-(4-Chloro-2-methylphenyl-imino)-4-(4-chloro-3-dimethylsulfamoylphenyl)-3-methyl-4-thiazoline hydrobromide Obtained by a procedure analogous to that indicated in Example 1 (b), from 2-(4-chloro-3-methylphenyl-imino)-4-(4-chloro-3-dimethylsulfamoylphenyl)-3-methylthiazolidin-4-ol hydrobromide in boiling glacial acetic acid, with subsequent precipitation with diethyl ether. Colorless crystals from glacial acetic acid; melting point 231° C. (with decomposition).

EXAMPLE 21

2-(4-Chloro-2-methylphenyl-imino)-4-(4-chloro-3-dimethylsulfamoylphenyl)-3-methyl-4-thiazoline Obtained by a procedure analogous to that indicated in Example 2 (a), from 2-(4-chloro-3-methylphenyl-imino)-4-(4-chloro-3-dimethylsulfamoylphenyl)-3-methyl-4-thiazoline hydrobromide and triethylamine. Melting point 137°–141° C.

EXAMPLE 22

2-(4-Chloro-3-dimethylsulfamoylphenyl)-2-(4-chlorophenyl-imino)-3-methyl-4-thiazoline hydrobromide (a) Obtained by a procedure analogous to that indicated in Example 1 (a), from 2-bromo-4'-chloro-3'-dimethylsulfamoylacetophenone and (4-chlorophenyl)-3-methylthiourea. Colorless crystals; melting point 244°–246° C. (with decomposition).

(b) Obtained by a procedure analogous to that of Example 1 (b), by boiling 2-(4-chloro-3-dimethylsulfamoylphenyl)-2-(4-chlorophenyl-imino)-3-methylthiazolidin-4-ol hydrobromide in glacial acetic acid for 2 hours. Melting point 246° C. (with decomposition).

EXAMPLE 23

4-(4-Chloro-3-dimethylsulfamoylphenyl)-2-(4-chlorophenyl-imino)-3-methyl-4-thiazoline Obtained by a procedure analogous to that indicated in Example 2 (a), from the hydrobromide of the title compound (Example 22) and triethylamine. Colorless crystals; melting point 184° C.

EXAMPLE 24

4-(4-Chloro-3-dimethylsulfamoylphenyl)-3-methyl-2-(2,3-dimethylphenyl-imino)-4-thiazoline hydrobromide Obtained by a procedure analogous to that indicated in Example 1 (b), from 4-(4-chloro-3-dimethylsulfamoylphenyl)-3-methyl-2-(2,3-dimethylphenyl-imino)-thiazolidin-4-ol hydrobromide, by boiling in glacial acetic acid for 2 hours and filtering off the crystals at room temperature. Colorless crystals from glacial acetic acid; melting point 256° C. (with decomposition).

EXAMPLE 25

4-(4-Chloro-3-dimethylsulfamoylphenyl)-3-methyl-2-(2,3-dimethylphenyl-imino)-4-thiazoline Obtained by a procedure analogous to that indicated in Example 2 (a), from 4-(4-chloro-3-dimethylsulfamoylphenyl)-3-methyl-2-(2,3-dimethylphenyl-imino)-4-thiazoline hydrobromide and triethylamine in methanol. Melting point 226° C.

EXAMPLE 26

2-(3-Chloro-2-methylphenyl-imino)-4-(4-chloro-3-dimethylsulfamoylphenyl)-3-methyl-4-thiazoline hydrobromide Obtained by a procedure analogous to that indicated in Example 1 (b), from 2-(3-chloro-2-methylphenyl-imino)-4-(4-chloro-3-dimethylsulfamoylphenyl)-3-methylthiazolidin-4-ol hydrobromide, by heating under reflux for 20 minutes in glacial acetic acid or by heating at 110° C. in propionic acid for 45 minutes. Colorless crystals; melting point 226°–228° C. (with decomposition).

EXAMPLE 27

2-(3-Chloro-2-methylphenyl-imino)-4-(4-chloro-3-dimethylsulfamoylphenyl)-3-methyl-4-thiazoline Obtained by a procedure analogous to that indicated in Example 2 (a), from 2-(3-chloro-2-methylphenyl-imino)-4-(4-chloro-3-dimethylsulfamoylphenyl)-3-methyl-4-thiazoline hydrobromide, the reaction mixture being rendered alkaline with a 20% methanolic ammonia solution instead of with triethylamine and worked up as in Example 2 (a). Colorless crystals; melting point 144°–146° C.

EXAMPLE 28

2-(4-Chloro-2-methoxyphenyl-imino)-4-(4-chloro-3-dimethylsulfamoylphenyl)-3-methyl-4-thiazoline hydrobromide Obtained by a procedure analogous to that indicated in Example 1 (b), from 2-(4-chloro-2-methoxyphenyl-imino)-4-(4-chloro-3-dimethylsulfamoylphenyl)-3-methylthiazolidin-4-ol hydrobromide, by boiling for 30 minutes in formic acid, then distilling off the solvent, treating the residue with ethyl acetate or diisopropyl ether and filtering off the solid. Melting point 244° C. (with decomposition).

EXAMPLE 29

2-(4-Chloro-2-methoxyphenyl-imino)-4-(4-chloro-3-dimethylsulfamoylphenyl)-3-methyl-4-thiazoline Obtained by a procedure analogous to that indicated in Example 2(a), from 2-(4-chloro-2-methoxyphenyl-imino)-4-(4-chloro-3-dimethylsulfamoylphenyl)-3-methyl-4-thiazoline hydrobromide. Colorless crystals; melting point 148°–150° C.

EXAMPLE 30

4-(4-Chloro-3-dimethylsulfamoylphenyl)-3-methyl-2-(3,4-methylenedioxyphenyl-imino(-4-thiazoline hydrobromide Obtained by a procedure analogous to that indicated in Example 1(b), from 4-(4-chloro-3-dimethylsulfamoylphenyl)-3-methyl-2-(3,4-methylenedioxyphenyl-imino)-thiazolidin-4-ol hydrobromide. Colorless crystals; melting point 230°–232° C. (with decomposition).

EXAMPLE 31

4-(4-Chloro-3-dimethylsulfamoylphenyl)-3-methyl-2-(3,4-methylenedioxyphenyl-imino)-4-thiazoline Obtained by a procedure analogous to that indicated in Example 27, from 4-(4-chloro-3-dimethylsulfamoylphenyl)-3-methyl-2-(3,4-methylenedioxyphenyl-imino)-4-thiazoline hydrobromide. Crystals with a melting point of 171°–173° C.

EXAMPLE 32

2-(3,4-Ethylenedioxyphenyl-imino)-4-(4-chloro-3-dimethylsulfamoylphenyl)-3-methyl-4-thiazoline hydrobromide (a) Obtained by a procedure analogous to that indicated in Example 1(a), from 2-bromo-4'-chloro-3'-dimethylsulfamoylacetophenone and 1-(3,4-ethylenedioxyphenyl)-3-methylthiourea. Colorless crystals; melting point 265°–267° C. (with decomposition).
or
(b) Obtained by a procedure corresponding to that indicated in Example 1(b), from 2-(3,4-ethylenedioxyphenyl-imino)-4-(4-chloro-3-dimethylsulfamoylphenyl)-3-methylthiazolidin-4-ol hydrobromide. Melting point 268° C. (with decomposition).

EXAMPLE 33

2-(3,4-Ethylenedioxyphenyl-imino)-4-(4-chloro-3-dimethylsulfamoylphenyl)-3-methyl-4-thiazoline Obtained by a procedure analogous to that indicated in Example 2(a), from 2-(3,4-ethylenedioxyphenyl-imino)-4-(chloro-3-dimethylsulfamoylphenyl)-3-methyl-4-thiazoline hydrobromide. Colorless crystals; melting point 200°–203° C.

EXAMPLE 34

4-(4-Chloro-3-dimethylsulfamoylphenyl)-3-methyl-2-(3,4,5-trimethoxyphenyl-imino)-4-thiazoline hydrobromide Obtained by a procedure analogous to that indicated in Example 1(b), from 4-(4-chloro-3-dimethylsulfamoylphenyl)-3-methyl-2-(3,4,5-trimethoxyphenyl-imino)-thiazolidin-4-ol hydrobromide, by boiling for 30 minutes in glacial acetic acid and precipitating with diisopropyl ether. Melting point 246° C.

EXAMPLE 35

4-(4-Chloro-3-dimethylsulfamoylphenyl)-3-methyl-2-(3,4,5-trimethoxyphenyl-imino)-4-thiazoline (a) Obtained by a procedure analogous to that indicated in Example 2(a), from 4-(4-chloro-3-dimethylsulfamoylphenyl)-3-methyl-2-(3,4,5-trimethoxyphenyl-imino)-4-thiazoline hydrobromide and triethylamine in methanol,
or
(b) by stirring in a mixture of 100 ml of ethyl acetate/50 ml of toluene and 100 ml of aqueous sodium bicarbonate solution at pH 8 to 8.5. The organic phase is separated off after 4 hours, the solvent is distilled off under a waterpump vacuum and the residue is treated with diisopropyl ether or water, so that the crystals can subsequently be filtered off. Melting point 119°–122° C.

EXAMPLE 36

4-(4-Chloro-3-dimethylsulfamoylphenyl)-2-(2,4-dichloro-5-methylphenyl-imino)-3-methyl-4-thiazoline hydrobromide Obtained by reacting 0.02 mole of 2-bromo-4'-chloro-3'-dimethylsulfamoylacetophenone with 0.02 mole of 1-(2,4-dichloro-5-methyl)-3-methylthiourea in 140 ml of acetone. The reaction mixture is stirred for 16 hours at room temperature and heated at the boil for 6 hours in a reaction vessel fitted with a reflux condenser, and after leaving to stand overnight at room temperature the crystals which have precipitated are filtered off. Melting point 242° C. (with decomposition).

EXAMPLE 37

3-Ethyl-4-(4-chloro-3-dimethylsulfamoylphenyl)-2-(2-methylphenyl-imino)-4-thiazoline hydrobromide (a) Obtained by a procedure analogous to that indicated in Example 1(a), from 2-bromo-4'-chloro-3'-dimethylsulfamoylacetophenone and 3-ethyl-1-(2-methylphenyl)-thiourea. Colorless crystals; melting point 280°–282° C. (with decomposition).
(b) Obtained by a procedure analogous to that indicated in Example 1(b), from 3-ethyl-4-(4-chloro-3-dimethylsulfamoylphenyl)-2-(2-methylphenyl-imino)-thiazolidin-4-ol hydrobromide. Melting point 281°–282° C. (with decomposition).

EXAMPLE 38

3-Ethyl-4-(4-chloro-3-dimethylsulfamoylphenyl)-2-(2-methylphenyl-imino)-4-thiazoline Obtained by a procedure analogous to that indicated in Example 2(a), from 3-ethyl-4-(4-chloro-3-dimethylsulfamoylphenyl)-2-(2-methylphenyl-imino)-4-thiazoline hydrobromide. Colorless crystals; melting point 164°–166° C.

EXAMPLE 39

4-(4-Chloro-3-dimethylsulfamoylphenyl)-2-phenylimino-3-propyl-4-thiazoline hydrobromide Obtained by a procedure analogous to that indicated in Example 1(b), from 4-(4-chloro-3-dimethylsulfamoylphenyl)-2-phenylimino-3-propylthiazolidin-4-ol hydrobromide. Colorless crystals; melting point 225° C. (with decomposition).

EXAMPLE 40

4-(4-Chloro-3-dimethylsulfamoylphenyl)-3-cyclopropyl-2-phenylimino-4-thiazoline hydrobromide (a) Obtained by a procedure analogous to that indicated in Example 1(a), from 1-cyclopropyl-3-phenylthiourea and 2-bromo-4'-chloro-3'-dimethylsulfamoylacetophenone, by stirring for 48 hours at room temperature in 200 ml of ethanol and then boiling for 2 hours in a vessel fitted with a reflux condenser, distilling off the solvent and filtering off the crystals after suspending in diisopropyl ether or ethyl acetate. Colorless crystals; melting point 260°–262° C. (with decomposition).

(b) Obtained by a procedure analogous to that of Example 1(b), from 4-(4-chloro-3-dimethylsulfamoylphenyl)-3-cyclopropyl-2-phenyl-iminothiazolidin-4-ol hydrobromide. Colorless crystals; melting point 259°–264° C. (with decomposition).

EXAMPLE 41

4-(4-Chloro-3-dimethylsulfamoylphenyl)-3-cyclopropyl-2-phenylimino-4-thiazoline

Obtained by a procedure analogous to that indicated in Example 2(a), from 4-(4-chloro-3-dimethylsulfamoylphenyl)-3-cyclopropyl-2-phenylimino-4-thiazoline hydrobromide. Melting point 156°–159° C.

EXAMPLE 42

3-sec.-Butyl-4-(4-chloro-3-dimethylsulfamoylphenyl)-2-phenylimino-4-thiazoline hydrobromide Obtained by a procedure analogous to that indicated in Example 1(a), from 2-bromo-4'-chloro-3'-dimethylsulfamoylacetophenone and 3-sec.-butyl-1-phenylthiourea, or by a procedure analogous to that of Example 1(b), from 3-sec.-butyl-4-(4-chloro-3-dimethylsulfamoylphenyl)-2-phenyliminothiazolidin-4-ol hydrobromide. Colorless crystals; melting point 250° C. (with decomposition).

EXAMPLE 43

3-sec.-Butyl-4-(4-chloro-3-dimethylsulfamoylphenyl)-2-phenylimino-4-thiazoline

Obtained by a procedure analogous to that indicated in Example 2(a) or 35(b), from 3-sec.-butyl-4-(4-chloro-3-dimethylsulfamoyl)-2-phenylimino-4-thiazoline hydrobromide. Colorless crystals; melting point 138° C.

EXAMPLE 44

4-(4-Chloro-3-dimethylsulfamoylphenyl)-3-n-hexyl-2-phenylimino-4-thiazoline hydrobromide Obtained (a) by a procedure analogous to that indicated in Example 1(a), from 2-bromo-4'-chloro-3'-dimethylsulfamoylacetophenone and 3-n-hexyl-1-phenylthiourea, or (b) by a procedure analogous to that indicated in Example 1(b), from 4-(4-chloro-3-dimethylsulfamoylphenyl)-3-n-hexyl-2-phenyliminothiazolidin-4-ol hydrobromide. Colorless crystals; melting point 234° C. (with decomposition).

EXAMPLE 45

4-(4-Chloro-3-dimethylsulfamoylphenyl)-3-n-hexyl-2-phenylimino-4-thiazoline

Obtained by a procedure analogous to that indicated in Example 2(a), from 4-(4-chloro-3-dimethylsulfamoylphenyl)-3-n-hexyl-2-phenylimino-4-thiazoline hydrobromide. Melting point 86° C.

EXAMPLE 46

4-(4-Chloro-3-dimethylsulfamoylphenyl-3-cyclohexyl-2-phenylimino-4-thiazoline hydrobromide Obtained by a procedure analogous to that indicated in Example 1(b), from 4-(4-chloro-3-dimethylsulfamoylphenyl)-3-cyclohexyl-2-phenyliminothiazolidin-4-ol hydrobromide. Colorless crystals; melting point 236° C.

EXAMPLE 47

4-(4-Chloro-3-dimethylsulfamoylphenyl)-3-cyclohexyl-2-phenylimino-4-thiazoline

Obtained by a procedure analogous to that indicated in Example 2(a) or 35(b), from 4-(4-chloro-3-dimethylsulfamoylphenyl)-3-cyclohexyl-2-phenylimino-4-thiazoline hydrobromide. Colorless crystals; melting point 148° C.

EXAMPLE 48

3-n-Butyl-4-(4-chloro-3-dimethylsulfamoylphenyl)-2-(2-methylphenyl-imino)-4-thiazoline hydrobromide Obtained (a) by a procedure analogous to that indicated in Example 1(a), from 3-n-butyl-1-phenylthiourea and 2-bromo-4'-chloro-3'-dimethylsulfamoylacetophenone, or (b) from 3-n-butyl-4-(4-chloro-3-dimethylsulfamoylphenyl)-2-(2-methylphenyl-imino)-thiazolidin-4-ol hydrobromide. Colorless crystals; melting point 238° C.

EXAMPLE 49

3-n-Butyl-4-(4-chloro-3-dimethylsulfamoylphenyl)-2-(2-methylphenyl-imino)-4-thiazoline Obtained by a procedure analogous to that indicated in Example 2(a), from 3-n-butyl-4-(4-chloro-3-dimethylsulfamoylphenyl)-2-(2-methylphenyl-imino)-4-thiazoline hydrobromide. Crystals; melting point 104° C.

EXAMPLE 50

4-(3-Diethylsulfamoyl-4-chlorophenyl)-3-methyl-2-phenyl-imino-4-thiazoline hydrochloride Obtained by boiling a suspension of 0.02 mole of 4-(3-diethylsulfamoyl-4-chlorophenyl)-3-methyl-2-phenyliminothiazolidin-4-ol for 2 hours in 120 ml of ethanol after acidifying with an ethereal HCl solution. The solvent is distilled off and the residue is crystallized under diisopropyl ether. Colorless crystals; melting point 222° C. (from ethanol/ether).

EXAMPLE 51

4-(3-Diethylsulfamoyl-4-chlorophenyl)-2-(4-chlorophenyl-imino)-3-methyl-4-thiazoline hydrobromide Obtained (a) by a procedure analogous to that indicated in Example 1(a), from 3'-diethylsulfamoyl-2-bromo-4'-chloroacetophenone and 1-(4-chlorophenyl)-3-methylthiourea, or (b) by a procedure analogous to that of Example 1(b), by boiling 4-(3-diethylsulfamoyl-4-chlorophenyl)-2-(4-chlorophenyl-imino)-3-methyl-thiazolidin-4-ol hydrobromide for 2 hours in glacial acetic acid and filtering off the crystals after cooling. Melting point 207° C. (with decomposition).

EXAMPLE 52

4-(3-Diethylsulfamoyl-4-chlorophenyl)-2-(4-chlorophenyl-imino)-3-methyl-4-thiazoline Obtained by a procedure analogous to that indicated in Example 2(a), from the corresponding hydrobromide (Example 51). Colorless crystals; melting point 198° C.

EXAMPLE 53

4-(3-Diethylsulfamoyl-4-chlorophenyl)-3-methyl-2-(2-methylphenyl-imino)-4-thiazoline hydrobromide Obtained by a procedure analogous to that indicated in Example 51(b), from 4-(3-diethylsulfamoyl-4-chlorophenyl)-3-methyl-2-(2-methylphenyl-imino)-thiazolidin-4-ol hydrobromide. Colorless crystals; melting point 258° (with decomposition).

EXAMPLE 54

4-(3-Diethylsulfamoyl-4-chlorophenyl)-3-methyl-2-(2-methylphenyl-imino)-4-thiazoline Obtained by a procedure analogous to that indicated in Example 2(a), from the corresponding hydrobromide (Example 53). Colorless crystals; melting point 166° C.

EXAMPLE 55

4-(3-N-Butyl-N-methylsulfamoyl-4-chlorophenyl)-3-methyl-2-phenylimino-4-thiazoline Obtained by a procedure analogous to that indicated in Example 2(b), from 4-(3-N-butyl-N-methylsulfamoyl-4-chlorophenyl)-3-methyl-2-phenyliminothiazolidin-4-ol. Colorless crystals; melting point 98°-100° C.

EXAMPLE 56

4-(3-N-Butyl-N-methylsulfamoyl-4-chlorophenyl)-3-methyl-2-phenylimino-4-thiazoline hydrochloride Obtained by a procedure analogous to that indicated in Example 3(c), from the thiazoline of Example 55. Colorless solid; melting point 84°-87° C. (with decomposition).

EXAMPLE 57

4-(4-Chloro-3-dipropylsulfamoylphenyl)-3-methyl-2-(2-methylphenyl-imino)-4-thiazoline hydrobromide Obtained by a procedure analogous to that indicated in Example 1(b), from 4-(4-chloro-3-dipropylsulfamoylphenyl)-3-methyl-2-(2-methylphenyl)-thiazolidin-4-ol hydrobromide, by boiling in glacial acetic acid for 2 hours. The reaction mixture is concentrated, water is added to the residue and the crystals are filtered off. Melting point 218°-220° C.

EXAMPLE 58

4-(4-Chloro-3-dipropylsulfamoylphenyl)-3-methyl-2-(2-methylphenyl-imino)-4-thiazoline Obtained by a procedure analogous to that indicated in Example 2(a), from the corresponding hydrobromide (Example 57) and triethylamine. Colorless crystals; melting point 114°-116° C.

EXAMPLE 59

4-(4-Chloro-3-dipropylsulfamoylphenyl)-3-methyl-2-(2,4-dimethylphenyl-imino)-4-thiazoline hydrobromide Obtained by a procedure analogous to that indicated in Example 51(b), from 4-(4-chloro-3-dipropylsulfamoylphenyl)-3-methyl-2-(2,4-dimethylphenyl)-thiazolidin-4-ol hydrobromide. Colorless crystals; melting point 239°-241° C. (with decomposition).

EXAMPLE 60

4-(4-Chloro-3-dipropylsulfamoylphenyl)-3-methyl-2-(2,4-dimethylphenyl-imino)-4-thiazoline Obtained by a procedure analogous to that indicated in Example 2(a), from the corresponding hydrobromide (Example 59). Colorless crystals; melting point 139°-141° C.

EXAMPLE 61

4-(4-Chloro-3-dipropylsulfamoylphenyl)-3-methyl-2-(2,3-dimethylphenyl-imino)-4-thiazoline hydrobromide Obtained by a procedure analogous to that indicated in Example 1(b), from 4-(4-chloro-3-dipropylsulfamoylphenyl)-3-methyl-2-(2,3-dimethylphenyl-imino)thiazolidin-4-ol hydrobromide by refluxing in glacial acetic acid, subsequently evaporating and crystallizing the viscous residue under water. Colorless crystals from methanol/ether; melting point 210°-212°.

EXAMPLE 62

4-(4-Chloro-3-dipropylsulfamoylphenyl)-3-methyl-2-(2,3-dimethylphenyl-imino)-4-thiazoline Obtained by a procedure analogous to that indicated in Example 2(a), from the hydrobromide of the title compound (Example 61). Colorless crystals; melting point 184°-187° C.

EXAMPLE 63

2-(5-Chloro-2,4-dimethoxyphenyl-imino)-4-(4-chloro-3-dipropylsulfamoylphenyl)-3-methyl-4-thiazoline hydrobromide Obtained by a procedure analogous to that indicated in Example 1(b), from 2-(5-chloro-2,4-dimethoxyphenyl-imino)-4-(4-chloro-3-dipropylsulfamoylphenyl)-3-methylthiazolidin-4-ol hydrobromide, by boiling in glacial acetic acid and stirring the residue under water after distilling off the solvent. Amorphous, glassy solid; melting point 130°-150° C.

EXAMPLE 64

2-(5-Chloro-2,4-dimethoxyphenyl-imino)-4-(4-chloro-3-dipropylsulfamoylphenyl)-3-methyl-4-thiazoline Obtained by a procedure analogous to that indicated in Example 2(a), from the corresponding hydrobromide. Colorless crystals; melting point 173°-175° C.

EXAMPLE 65

4-(4-Chloro-3-N-morpholinosulfamoylphenyl)-3-methyl-2-phenylimino-4-thiazoline

Obtained by a procedure analogous to that indicated in Example 2(b), from 4-(4-chloro-3-N-morpholinosulfonylphenyl)-3-methyl-2-phenyliminothiazolidin-4-ol by boiling in glacial acetic acid and precipitating with diisopropyl ether. Melting point 212°-214° C.

EXAMPLE 66

4-[4-Chloro-3-(1-methyl-4-piperazinylsulfonyl)-phenyl]-3-methyl-2-phenylimino-4-thiazoline Obtained by a procedure analogous to that indicated in Example 2(b), from 4-[4-chloro-3-(1-methyl-4-piperazinylsulfonyl)-phenyl]-3-methyl-2-phenyliminothiazolidin-4-ol, by boiling with glacial acetic acid and subsequently distilling off the solvent. Water is added to the residue and the pH is adjusted to 13 with 2 N NaOH. The crystals are filtered off and recrystallized from isopropanol. Melting point 156°–158° C.

EXAMPLE 67

4-[4-Chloro-3-(3,5-dimethylmorpholino-N-sulfonyl)-phenyl]-3-methyl-2-phenylimino-4-thiazoline Obtained by a procedure analogous to that indicated in Example 2(b), from 4-[4-chloro-3-(3,5-dimethylmorpholino-N-sulfonyl)-phenyl]-3-methyl-2-phenylimino-4-thiazoline. Colorless crystals; melting point 190°–192° (from ethanol).

The thiazolines of the formula I which are listed in the examples which follow are obtained from the correspondingly substituted thiazolidin-4-ol derivatives IV by a procedure analogous to that described in Example 2(b):

EXAMPLE 68

4-(4-Chloro-3-cyclopropylsulfamoylphenyl)-3-methyl-2-phenylimino-4-thiazoline, melting point 176° C.

EXAMPLE 69

4-(4-Chloro-3-cyclohexylsulfamoylphenyl)-3-methyl-2-phenylimino-4-thiazoline, decomposition temperature 143° C.

EXAMPLE 70

4-[4-Chloro-3-(4-methylbenzylsulfamoyl)-phenyl]-3-methyl-2-phenylimino-4-thiazoline, melting point 164°–169° C.

EXAMPLE 71

4-(4-Chloro-3-n-propylsulfamoylphenyl)-3-methyl-2-phenylimino-4-thiazoline, melting point 157°–160° C.

EXAMPLE 72

4-[4-Chloro-3-(4-chlorobenzylsulfamoyl)-phenyl]-3-methyl-2-phenylimino-4-thiazoline, melting point 246°–247° C.

EXAMPLE 73

4-(4-Chloro-3-sulfamoylphenyl)-3-methyl-2-phenylimino-4-thiazoline, melting point 170°–173° C.

The thiazoline derivatives of the formula I which are listed in the examples which follow are obtained from the correspondingly substituted thiazolidin-4-ol derivatives IV by a procedure analogous to that described in Example 1(b):

EXAMPLE 74

4-(4-Chloro-3-sulfamoylphenyl)-3,5-dimethyl-2-phenylimino-4-thiazoline hydrobromide, decomposition temperature 219° C.

EXAMPLE 75

4-(4-Bromo-3-sulfamoylphenyl)-2-(4-methoxyphenyl-imino)-3-methyl-4-thiazoline hydrobromide, melting point 273° C.

EXAMPLE 76

4-(4-Chloro-3-sulfamoylphenyl)-2-(3,4,5-trimethoxyphenylimino)-3-methyl-4-thiazoline hydrobromide, melting point 294° (with decomposition).

EXAMPLE 77

2-(3,4-Ethylenedioxyphenyl-imino)-4-(4-chloro-3-sulfamoylphenyl)-3-methyl-4-thiazoline hydrobromide, melting point 283° C. (with decomposition).

EXAMPLE 78

4-(4-Chloro-3-sulfamoylphenyl)-2-(3,4-methylenedioxyphenyl-imino)-3-methyl-4-thiazoline hydrobromide, melting point 275° C. (with decomposition).

EXAMPLE 79

4-(4-Chloro-3-sulfamoylphenyl)-2-(4-methoxyphenyl-imino)-3-methyl-4-thiazoline hydrobromide, melting point 277°–280° C. (with decomposition).

EXAMPLE 80

3-Ethyl-4-(4-chloro-3-sulfamoylphenyl)-2-phenylimino-4-thiazoline hydrochloride, melting point 241° C. (with decomposition).

EXAMPLE 81

4-(4-Chloro-3-sulfamoylphenyl)-2-(4-isopropyl-phenylimino)-3-methyl-4-thiazoline hydrochloride, melting point 276°–278° C. (with decomposition).

EXAMPLE 82

4-(4-Chloro-3-sulfamoylphenyl)-3-methyl-2-(2,3-dimethylphenyl-imino)-4-thiazoline hydrochloride, melting point 240° C. (with decomposition).

EXAMPLE 83

2-(2-Chlorophenyl-imino)-4-(4-chloro-3-sulfamoylphenyl)-3-methyl-4-thiazoline hydrochloride, melting point 245°–247° C.

EXAMPLE 84

2-(4-Chloro-2-methoxyphenyl-imino)-4-(4-chloro-3-sulfamoylphenyl)-3-methyl-4-thiazoline hydrochloride, melting point 234°–237° C. (with decomposition).

EXAMPLE 85

2-(5-Chloro-2,4-dimethoxyphenyl-imino)-4-(4-chloro-3-sulfamoylphenyl)-3-methyl-4-thiazoline hydrobromide, melting point 278°–279° C. (with decomposition).

EXAMPLE 86

4-(4-Chloro-3-sulfamoylphenyl)-3-methyl-2-(3-dimethylaminophenyl-imino)-4-thiazoline hydrobromide, melting point 258°–260° (with decomposition).

EXAMPLE 87

4-(4-Chloro-3-sulfamoylphenyl)-3-methyl-2-(2,4-dimethylphenyl-imino)-4-thiazoline hydrobromide, melting point 255°–258° C. (with decomposition).

EXAMPLE 88

2-(2-Ethoxy-5-methylphenylimino)-4-(4-chloro-3-sulfamoylphenyl)-3-methyl-4-thiazoline hydrobromide, melting point 227°–230° C.

EXAMPLE 89

4-(4-Chloro-3-sulfamoylphenyl)-2-(2-methoxy-4,5-dimethylphenyl-imino)-3-methyl-4-thiazoline hydrobromide, melting point 257°–260° C.

EXAMPLE 90

4-(4-Chloro-3-sulfamoylphenyl)-3-methyl-2-(3-trifluoromethylphenyl-imino)-4-thiazoline hydrobromide, melting point 217° C. (with decomposition).

EXAMPLE 91

4-(4-Chloro-3-sulfamoylphenyl)-2-(4-fluorophenylimino)-3-methyl-4-thiazoline hydrobromide

EXAMPLE 92

3-Ethyl-4-(4-chloro-3-sulfamoylphenyl)-2-(4-methylphenyl-imino)-4-thiazoline hydrobromide, melting point 268° C. (with decomposition).

EXAMPLE 93

2-(4-Ethoxyphenyl-imino)-4-(4-chloro-3-sulfamoylphenyl)-3-methyl-4-thiazoline hydrobromide, melting point 263° C. (with decomposition).

The thiazoline derivatives of the formula I which are listed in the examples which follow are obtained from the correspondingly substituted thiazolidin-4-ol derivatives of the general formula IV by a procedure analogous to that indicated in Examples 3(b) and 50:

EXAMPLE 94

4-(3-n-Butylsulfamoyl-4-chlorophenyl)-3-methyl-2-phenylimino-4-thiazoline hydrochloride, melting point 237° C.

EXAMPLE 95

4-(3-Benzylsulfamoyl-4-chlorophenyl)-3-methyl-2-phenylimino-4-thiazoline hydrochloride, decomposition temperature 152° C.

EXAMPLE 96

4-(3-N-Benzyl-N-methylsulfamoyl-4-chlorophenyl)-3-methyl-2-phenylimino-4-thiazoline hydrochloride, decomposition temperature 165° C. (from ethanol).

EXAMPLE 97

4-[4-Chloro-3-(2,4-dimethoxybenzylsulfamoyl)-phenyl]-3-methyl-2-phenylimino-4-thiazoline hydrochloride, decomposition temperature 158° C.

EXAMPLE 98

4-[3-(2-Chlorobenzylsulfamoyl)-4-chlorophenyl]-3-methyl-2-phenylimino-4-thiazoline hydrochloride, melting point 264° C.

EXAMPLE 99

4-(4-Chloro-3-cyclopentylsulfamoyl-phenyl)-3-methyl-2-phenyl-imino-4-thiazoline hydrochloride, melting point 257° C. (with decomposition).

EXAMPLE 100

4-(3-Ethylsulfamoyl-4-chlorophenyl)-3-methyl-2-phenylimino-4-thiazoline hydrochloride, melting point 240°–241° C. (with decomposition).

EXAMPLE 101

4-[4-Chloro-3-(4-methoxybenzylsulfamoyl)-phenyl]-3-methyl-2-phenylimino-4-thiazoline hydrochloride, decomposition temperature 133°–137° C.

EXAMPLE 102

4-[4-Chloro-3-(3,5-dimethyl-1-piperidylsulfonyl)-phenyl]-3-methyl-2-phenylimino-4-thiazoline hydrochloride, melting point 198° C.

EXAMPLE 103

4-(4-Chloro-3-sulfamoylphenyl)-3-methyl-2-(2-methylphenyl-imino)-4-thiazoline hydrochloride, melting point 278° C. (with decomposition).

EXAMPLE 104

4-(4-Chloro-3-sulfamoylphenyl)-3-methyl-2-(4-methylphenyl-imino)-4-thiazoline hydrobromide 0.02 mole (9.8 g) of 4-(4-chloro-3-sulfamoylphenyl)-3-methyl-2-(4-methylphenyl-imino)-thiazolidin-4-ol hydrobromide are boiled in 120 ml of ethanol for 2 hours under reflux. After cooling to room temperature, 200 ml of diisopropyl ether are added and the crystals are filtered off. Melting point 265° C. (with decomposition).

The thiazoline derivatives of the formula I which are listed in the examples which follow are obtained from the correspondingly substituted thiazolidin-4-ol derivatives of the general formula IV by a procedure analogous to that indicated in Example 104:

EXAMPLE 105

2-(2-Ethylphenyl-imino)-4-(4-chloro-3-sulfamoylphenyl)-3-methyl-4-thiazoline hydrochloride, decomposition temperature 176° C.

EXAMPLE 106

2-(2-Ethylphenyl-imino)-4-(4-chloro-3-sulfamoylphenyl)-3-methyl-4-thiazoline hydrobromide, decomposition temperature 178° C.

EXAMPLE 107

4-(4-Chloro-3-methylsulfamoylphenyl)-3-methyl-2-(2,3-dimethylphenyl-imino)-4-thiazoline hydrobromide, melting point 270° (with decomposition).

EXAMPLE 108

4-[4-Chloro-3-(1-piperidinylsulfonyl)-phenyl]-3-methyl-2-phenylimino-4-thiazoline hydrochloride, melting point 187°–191° C.

EXAMPLE 109

4-[4-Chloro-3-(1-pyrrolidinylsulfonyl)-phenyl]-3-methyl-2-phenylimino-4-thiazoline hydrochloride, melting point 162° C. (with decomposition).

EXAMPLE 110

4-[4-Chloro-3-(1-n-dodecylsulfamoyl)-phenyl]-3-methyl-2-phenylimino-4-thiazoline hydrochloride, melting point 128° C. (with decomposition).

EXAMPLE 111

4-(4-Chloro-3-sulfamoylphenyl)-2-phenylimino-3-propyl-4-thiazoline hydrobromide, melting point 198° C. (with decomposition).

EXAMPLE 112

3-Allyl-4-(4-chloro-3-sulfamoylphenyl)-2-phenylimino-4-thiazoline hydrobromide, melting point 248°–252° C. (with decomposition).

EXAMPLE 113

3-sec.-Butyl-4-(4-chloro-3-sulfamoylphenyl)-2-phenylimino-4-thiazoline hydrobromide, melting point 265°–268° C. (with decomposition).

EXAMPLE 114

4-[4-Chloro-3-(1-n-hexylsulfamoyl)-phenyl]-3-methyl-2-phenylimino-4-thiazoline hydrochloride, melting point 177°–182° C. (with decomposition).

EXAMPLE 115

2-(4-Diethylaminophenyl-imino)-4-(4-chloro-3-sulfamoylphenyl)-3-methyl-4-thiazoline hydrochloride, decomposes above 180° C.

The basic compounds of the formula I which are listed in the examples which follow can be obtained from the acid addition salts of the compounds of the formula I by the action of a base, by a procedure analogous to those indicated in Examples 2(a), 27 and 35(b):

EXAMPLE 116

4-(4-Chloro-3-sulfamoylphenyl)-3,5-dimethyl-2-phenylimino-4-thiazoline, decomposes above 117° C.

EXAMPLE 117

4-(4-Bromo-3-sulfamoylphenyl)-2-(4-methoxyphenyl-imino)-3-methyl-4-thiazoline, melting point 197° C. (from alcohol).

EXAMPLE 118

2-(2-Ethylphenyl-imino)-4-(4-chloro-3-sulfamoylphenyl)-3-methyl-4-thiazoline, melting point 161°–163° C.

EXAMPLE 119

4-(4-Chloro-3-sulfamoylphenyl)-3-methyl-2-(4-methylphenyl-imino)-4-thiazoline, melting point 267° C.

EXAMPLE 120

4-[4-Chloro-3-(1-piperidylsulfonyl)-phenyl]-3-methyl-2-phenylimino-4-thiazoline, melting point 189°–195° C.

EXAMPLE 121

4-[4-Chloro-3-(1-pyrrolidinylsulfonyl)-phenyl]-3-methyl-2-phenylimino-4-thiazoline, melting point 191°–194° C.

EXAMPLE 122

4-(4-Chloro-3-sulfamoylphenyl)-2-phenylimino-3-propyl-4-thiazoline, melting point 165°–170° C.

EXAMPLE 123

3-sec.-Butyl-4-(4-chloro-3-sulfamoylphenyl)-2-phenylimino-4-thiazoline, melting point 80° C.

EXAMPLE 124

4-[3-(1-Butylsulfamoyl)-4-chlorophenyl]-3-methyl-2-phenylimino-4-thiazoline, melting point 130°–135° C.

EXAMPLE 125

4-(3-Diethylsulfamoyl-4-chlorophenyl)-3-methyl-2-phenylimino-4-thiazoline, melting point 173°–175° C.

EXAMPLE 126

4-(4-Chloro-3-sulfamoylphenyl)-3-methyl-2-(3,4,5-trimethoxy-phenyl-imino)-4-thiazoline, melting point 187°–189° C.

EXAMPLE 127

2-(3,4-Ethylenedioxyphenyl-imino)-4-(4-chloro-3-sulfamoylphenyl)-3-methyl-4-thiazoline, melting point 247°–249° C.

EXAMPLE 128

4-(4-Chloro-3-sulfamoylphenyl)-2-(3,4-methylenedioxyphenyl-imino)-3-methyl-4-thiazoline, melting point 187°–189° C.

EXAMPLE 129

4-(4-Chloro-3-sulfamoylphenyl)-2-(4-methoxyphenylimino)-3-methyl-4-thiazoline, melting point 210°–214° C.

EXAMPLE 130

4-(4-Chloro-3-sulfamoylphenyl)-2-(4-fluorophenylimino)-3-methyl-4-thiazoline, melting point 234°–236° C.

EXAMPLE 131

2-(4-Ethoxyphenyl-imino)-3-methyl-4-(4-chloro-3-sulfamoylphenyl)-4-thiazoline, melting point 233° C.

EXAMPLE 132

4-(4-Chloro-3-sulfamoylphenyl)-3-methyl-2-(3-methylphenyl-imino)-4-thiazoline, melting point 193°–194° (from methanol).

EXAMPLE 133

2-(5-Chloro-2,4-dimethoxyphenyl-imino)-4-(4-chloro-3-sulfamoylphenyl)-3-methyl-4-thiazoline, melting point 204°–206° C.

EXAMPLE 134

4-(4-Chloro-3-sulfamoylphenyl)-3-methyl-2-(3-dimethylaminophenyl-imino)-4-thiazoline, melting point 134°–140° C.

EXAMPLE 135

4-(4-Chloro-3-sulfamoylphenyl)-3-methyl-2-(2,4-dimethylphenyl-imino)-4-thiazoline, melting point 270°–275° C.

EXAMPLE 136

2-(2-Ethoxy-5-methylphenyl-imino)-4-(4-chloro-3-sulfamoylphenyl)-3-methyl-4-thiazoline, melting point 194°–197° C.

EXAMPLE 137

4-(4-Chloro-3-chlorosulfonylphenyl)-3-methyl-2-phenyliminothiazolidin-4-ol hydrobromide A solution of 3-methyl-1-phenylthiourea is added to a solution of 6.64 g (0.02 mole) of 2-bromo-4'-chloro-3'-chlorosulfonylacetophenone in 40 ml of acetone, with stirring, and, after moderate evolution of heat, the crystalline title compound precipitates out. The reaction mixture is stirred for a further 4 hours at room temperature and is then cooled to 0° C. and the colorless crystals are filtered off.

1. Decomposition temperature 220° C., with resolidification.
2. Melting point 264°–265° C., with decomposition.

The following compounds of the formula XII in which Z is halogen are obtained, for example, from the correspondingly substituted compounds of the formula II in which Z is halogen and the thioureas of the formula III, by a procedure analogous to that indicated in Example 137.
(a) 4-(4-Chloro-3-chlorosulfonylphenyl)-2-(4-methoxyphenyl-imino)-3-methylthiazolidin-4-ol hydrobromide,
(b) 4-(4-Chloro-3-chlorosulfonylphenyl)-3-methyl-2-(2-methylphenyl-imino)-thiazolidin-4-ol hydrobromide, melting point 236°–238° C. (with decomposition)
(c) 4-(4-Chloro-3-chlorosulfonylphenyl)-2-(2-chlorophenyl-imino)-3-methylthiazolidin-4-ol hydrobromide,
(d) 4-(4-Chloro-3-chlorosulfonylphenyl)-3-methyl-2-(2,4-dimethylphenyl-imino)-thiazolidin-4-ol hydrobromide
(e) 3-Ethyl-4-(4-chloro-3-chlorosulfonylphenyl)-2-(2-methylphenylimino)-thiazolidin-4-ol hydrobromide
(f) 2-(2,4-Diethylphenyl-imino)-4-(4-chloro-3-chlorosulfonylphenyl)-3-methylthiazolidin-4-ol hydrobromide,
(g) 4-(4-Chloro-3-chlorosulfonylphenyl)-2-(4-chlorophenyl-imino)-3-methylthiazolidin-4-ol hydrobromide,
(h) 4-(4-Chloro-3-chlorosulfonylphenyl)-2-(4-fluorophenyl-imino)-3-methylthiazolidin-4-ol hydrobromide.

EXAMPLE 138

4-(4-Chloro-3-methylsulfamoylphenyl)-2-(4-methoxyphenylimino)-3-methyl-4-thiazoline hydrochloride 10.6 g (0.02 mole) of 4-(4-chloro-3-chlorosulfonylphenyl)-2-(4-methoxyphenyl-imino)-3-methylthiazolidin-4-ol hydrobromide are introduced into a mixture of 10 ml of 40% strength aqueous methylamine and 150 ml of methanol and the resulting mixture is stirred for 20 hours at room temperature. The solvent is distilled off, the residue is taken up in 100 ml of ethanol and this solution is acidified with methanolic or ethanolic hydrogen chloride solution and heated at the boil for 2 hours. The solvent is distilled off, the residue is crystallized under ether, ethyl acetate or diisopropyl ether and the crystals are filtered off. Melting point 257° C. (with decomposition) (from isopropanol).

The compounds of the formula I which are described below are obtained, for example, from the correspondingly substituted compounds of the formula XII in which Z is halogen on reaction with a correspondingly substituted amine HNR$^6$R$^7$ or ammonia, by a procedure analogous to that indicated in Example 138:

EXAMPLE 139

4-(4-Chloro-3-sulfamoylphenyl)-3-methyl-2-(4-methoxyphenyl-imino)-4-thiazoline hydrochloride, melting point 267° C. (with decomposition).

EXAMPLE 140

4-(4-Chloro-3-sulfamoylphenyl)-3-methyl-2-phenylimino-4-thiazoline hydrochloride, melting point 242° C. (with decomposition) (from methanol).

EXAMPLE 141

4-(4-Chloro-3-dimethylsulfamoylphenyl)-3-methyl-2-phenyl-imino-4-thiazoline hydrochloride, melting point 228°–231° C. (with decomposition).

EXAMPLE 142

4-(3-n-Butylsulfamoyl-4-chlorophenyl)-2-(4-methoxyphenyl-imino)-3-methyl-4-thiazoline hydrochloride, decomposes above 102° C.

EXAMPLE 143

4-(4-Chloro-3-(1-hexylsulfamoyl)-phenyl)-2-(4-methoxyphenyl-imino)-3-methyl-4-thiazoline hydrochloride, decomposes above 98° C.

EXAMPLE 144

4-(3-Benzylsulfamoyl-4-chlorophenyl)-2-(4-methoxyphenylimino)-3-methyl-4-thiazoline hydrochloride, decomposes above 135° C.

The further acid addition salts of the formula I described in the examples which follow are obtained by the action of proton acids of the formula HA on the basic compounds of the formula I, by a procedure analogous to that indicated in Example 3(c):

EXAMPLE 146

4-(4-Chloro-3-sulfamoylphenyl)-3-methyl-2-(3-trifluoromethylphenyl-imino)-4-thiazoline hydrochloride, melting point 222° C.

EXAMPLE 147

4-(4-Chloro-3-n-propylsulfamoylphenyl)-3-methyl-2-phenylimino-4-thiazoline hydrochloride, melting point 239° C.

EXAMPLE 148

4-[4-Chloro-3-(4-methylbenzylsulfamoyl)-phenyl]-3-methyl-2-phenylimino-4-thiazoline, melting point 92°–100° C.

EXAMPLE 149

4-(4-Chloro-3-sulfamoylphenyl)-2-(4-methoxyphenylimino)-3-methyl-4-thiazoline hydrochloride, melting point 276° C.

EXAMPLE 150

4-(4-Chloro-3-dimethylsulfamoylphenyl)-3-methyl-2-phenyl-imino-4-thiazoline amidosulfonate, melting point 296°–298° C.

EXAMPLE 151

4-(4-Chloro-3-dimethylsulfamoylphenyl)-3-methyl-2-(2,4-dimethylphenyl-imino)-4-thiazoline hydrobromide 3.41 g (0.01 mole) of 2-bromo-4'-chloro-3'-dimethylsulfamoyl-acetophenone are added to a solution of 1.83 g (0.01 mole) of 3-methyl-1-(2,4-dimethylphenyl)thiourea in 60 ml of glacial acetic acid and the mixture is stirred at room temperature for 20 minutes. It is then boiled for 20 minutes under a reflux condenser and allowed to cool, 60 ml of ethyl acetate or diisopropyl ether are added to the reaction mixture and the crystals are filtered off. Melting point 260°–264° C. (with decomposition).

EXAMPLE 152

4-(4-Chloro-3-chlorosulfonylphenyl)-3-methyl-2-phenylimino-4-thiazoline hydrobromide 2.5 g (50 mmoles) of 4-(4-chloro-3-chlorosulfonylphenyl)-3-methyl-2-phenyliminothiazolidin-4-ol hydrobromide are heated rapidly in a jacket, which has been preheated to 220° C., in vacuo (0.1 mm Hg) over phosphorus pentoxide. The substance melts with foaming, as a result of the elimination of water, and solidifies immediately after the end of the reaction, with recrystallization. Slightly green colored crystals; melting point 264° C.

The following thiazoline derivatives of the formula XI are obtained, for example, from the correspondingly substituted thiazolidin-4-ol derivatives of the general formula XII, by a procedure analogous to that indicated in Example 152

(a) 4-(4-Chloro-3-chlorosulfonylphenyl)-2-(4-methoxyphenyl-imino)-3-methyl-4-thiazoline hydrobromine
(b) 4-(4-Chloro-3-chlorosulfonylphenyl)-3-methyl-2-(2-methylphenyl-imino)-4-thiazoline hydrobromide, melting point 250° C. (with decomposition)
(c) 4-(4-Chloro-3-chlorosulfonylphenyl)-2-(2-chlorophenyl-imino)-3-methyl-4-thiazoline hydrobromide
(d) 4-(4-Chloro-3-chlorosulfonylphenyl)-3-methyl-2-(2,4-dimethylphenyl-imino)-4-thiazoline hydrobromide
(e) 3-Ethyl-4-(4-chloro-3-chlorosulfonylphenyl)-2-(2-methylphenylimino)-4-thiazoline hydrobromide
(f) 2-(2,4-Diethylphenyl-imino)-4-(4-chloro-3-chlorosulfonylphenyl)-3-methyl-4-thiazoline hydrobromide
(g) 4-(4-Chloro-3-chlorosulfonylphenyl)-2-(4-chlorophenyl-imino)-3-methyl-4-thiazoline hydrobromide
(h) 4-(4-Chloro-3-chlorosulfonylphenyl)-2-(4-fluorophenyl-imino)-3-methyl-4-thiazoline hydrobromide

EXAMPLE 153

4-(4-Chloro-3-dimethylsulfamoylphenyl)-3-methyl-2-phenylimino-4-thiazoline 4.8 g (0.01 mole) of 4-(4-chloro-3-chlorosulfonylphenyl)-3-methyl-2-phenylimino-4-thiazoline hydrobromide are added in portions to a mixture of 5 ml (about 0.05 mole) of 40% strength aqueous dimethylamine solution and 50 ml of methanol (or ethanol), with external cooling and stirring, at a rate such that the temperature as far as possible does not rise above 35° C. The reaction mixture is stirred for 14 hours at room temperature, the solvent is distilled off under a water-pump vacuum and the residue is crystallized under 50 ml of water, stirring with a magnetic stirrer. Colorless crystals; melting point 178°–181° C.

The following thiazoline derivatives of the formula I are obtained, for example, from the correspondingly substituted compounds of the formula XI and a correspondingly substituted amine of the formula $HNR^6R^7$ or ammonia, by a procedure analogous to that indicated in Example 153:

(a) 4-(3-Diethylsulfamoyl-4-chlorophenyl)-3-methyl-2-phenyl-imino-4-thiazoline
(b) 4-(4-Chloro-3-sulfamoylphenyl)-3-methyl-2-phenylimino-4-thiazoline
(c) 3-Ethyl-4-(4-chloro-3-dimethylsulfamoylphenyl)-2-phenylimino-4-thiazoline
(d) 4-(4-Chloro-3-dimethylsulfamoylphenyl)-3-methyl-2-(2-methylphenylimino)-4-thiazoline
(e) 4-(3-Diethylsulfamoyl-4-chlorophenyl)-3-methyl-2-(2-methylphenylimino)-4-thiazoline
(f) 4-(4-Chloro-3-dimethylsulfamoylphenyl)-3-methyl-2-(2-chlorophenyl-imino)-4-thiazoline
(g) 4-(4-Chloro-3-dimethylsulfamoylphenyl)-3-methyl-2-(4-methoxyphenyl-imino)-4-thiazoline
(h) 4-(4-Chloro-3-dimethylsulfamoylphenyl)-3-methyl-2-(2,4-dimethylphenyl-imino)-4-thiazoline
(i) 4-(4-Chloro-3-dimethylsulfamoylphenyl)-2-(4-chlorophenyl-imino)-3-methyl-4-thiazoline
(j) 4-(4-Chloro-3-dimethylsulfamoylphenyl)-2-(4-fluorophenyl-imino)-3-methyl-4-thiazoline

EXAMPLE 154

4-(4-Chloro-3-dimethylsulfamoylphenyl)-3-methyl-2-phenylimino-4-thiazoline 0.01 mole of 4-(4-chloro-3-sulfamoylphenyl)-3-methyl-2-phenylimino-4-thiazoline or its hydrochloride are suspended in a mixture of 110 ml of toluene and 50 ml of water and the pH of the aqueous phase is adjusted to 13–14 with 2 N NaOH. After adding catalytic amounts of benzyl-triethyl-ammonium chloride as a phase transfer catalyst and 0.024 mole of dimethyl sulfate, the reaction mixture is heated to 80° to 90° C., with stirring and maintaining the pH value, and dimethyl sulfate is added in approximately 1 g portions at approximately 2 hour intervals until the thin layer chromatogram on silica gel (1:1 toluene/ethyl acetate) indicates complete conversion. The organic phase is stirred with aqueous ammonia solution for 4 hours at 40°, in order to decompose any amounts of dimethyl sulfate which may be present, and dried over sodium sulfate and the solvent is distilled off. Colorless crystals, melting point 179°–180° C. (from glacial acetic acid).

EXAMPLE 155

(A)

4-(4-Chloro-3-sulfamoylphenyl)-3-methyl-2-phenyliminothiazolidin-4-ol hydrobromide A solution of 3.13 g (0.01 mole) of 2-bromo-4'-chloro-3'-sulfamoylacetophenone in 50 ml of acetone is added to a solution of 1.66 g (0.01 mole) of 3-methyl-1-phenyl-thiourea in 100 ml of acetone, whilst stirring with a magnetic stirrer; during this addition the reaction temperature should not rise above 30° C. After stirring for 5 hours at room temperature, the crystals are filtered off. Melting point 164° C. (with decomposition).

(B)

4-(4-Chloro-3-sulfamoylphenyl)-3-methyl-2-phenyliminothiazolidin-4-ol (a) 4.8 g (0.01 mole) of 4-(4-chloro-3-sulfamoylphenyl)-3-methyl-2-phenyliminothiazolidin-4-ol hydrobromide in 70 ml of methanol are cooled to 0° C. and, after adding 3 ml of triethylamine, the mixture is stirred at room temperature for 30 minutes to 1 hour. The methanol is distilled off under mild conditions in vacuo, the bath temperature being kept below 40° C., the residue is stirred in water for 30 minutes and the crystals are filtered off. Melting point 125°–129° C. (with decomposition).

(b) 5 g (0.01 mole) of 4-(4-chloro-3-chlorosulfonylphenyl)-3-methyl-2-phenyliminothiazolidin-4-ol hydrobromide are introduced into a mixture of 50 ml of methanol and 5 ml of 20% strength aqueous ammonia and the resulting mixture is stirred for 3 hours at room temperature. The solvent is distilled off under mild conditions in vacuo, the bath temperature being kept below 40° C., the residue is stirred in water for 30 minutes and the crystals are filtered off. Melting point 126°–129° C. (with decomposition).

(C)
4-(4-Chloro-3-sulfamoylphenyl)-3-methyl-2-phenylimino-thiazolidin-4-ol hydrochloride 4 g (0.01 mole) of 4-(4-chloro-3-sulfamoylphenyl)-3-methyl-2-phenyliminothiazolidin-4-ol in 50 ml of acetone, ethyl acetate or ether are acidified with ethereal hydrogen chloride solution and, after stirring at room temperature for 1 to 3 hours, the crystals are filtered off. Melting point 179° C. (with decomposition).

The compounds of the formula IV listed in Table 4 which follows are obtained by a procedure analogous to that of Example 155.

TABLE 4

(Legend: Me = methyl, Et = ethyl, Prop = propyl, But = butyl, Pent = pentyl, Hex = hexyl, Bz = benzyl, i = iso, sec. = secondary, c = cyclo. The substituent Y is in the 4-position on the phenyl radical, the thiazole ring being taken as in the 1-position and the sulfamoyl radical as in the 3-position)

| Example No. | $R^1$ | $R^2$ | $R^3$ | $R^4$ | $R^5$ | $R^6$ | $R^7$ | Y | HA | Melting point*1 °C. |
|---|---|---|---|---|---|---|---|---|---|---|
| 156 | Me | 2-Me | 4-Me | H | H | Me | Me | Cl | HBr | 257 |
| 157 | Me | 2-Me | 4-Cl | H | H | Me | Me | Cl | HBr | 223 |
| 158 | Me | 4-F | H | H | H | Me | Me | Cl | HBr | 247 |
| 159 | Me | 2-Et | H | H | H | Me | Me | Cl | HBr | 276 |
| 160 | But | 2-Me | H | H | H | Me | Me | Cl | HBr | 239 |
| 161 | Me | 2-OMe | 4-Cl | H | H | Me | Me | Cl | HBr | 242 |
| 162 | Me | H | H | H | H | —(CH$_2$)$_2$—O—(CH$_2$)$_2$— | | Cl | — | 130 |
| 163 | Me | 2-Me | 3-Cl | H | H | Me | Me | Cl | HBr | 223 |
| 164 | Me | 4-NEt$_2$ | H | H | H | Me | Me | Cl | HBr | 223 |
| 165 | Me | H | H | H | H | —(CH$_2$)$_2$—N(Me)—(CH$_2$)$_2$— | | Cl | — | 148 |
| 166 | Me | H | H | H | H | H | c-Prop | Cl | — | 107 |
| 167 | Me | H | H | H | H | H | c-Pent | Cl | — | 178 |
| 168 | Me | H | H | H | H | H | c-Pent | Cl | HCl | |
| 169 | Me | H | H | H | H | —CH$_2$—CH(Me)—O—CH$_2$—CH(Me)— | | Cl | — | 125 |
| 170 | Me | H | H | H | H | H | c-Hex | Cl | — | 113 |
| 171 | Me | 3-Me | H | H | H | H | H | Cl | HBr | 178 |
| 172 | Me | 2-Me | 3-Me | H | H | Prop | Prop | Cl | HBr | 211 |
| 173 | Me | H | H | H | H | H | Et | Cl | — | 140 |
| 174 | Me | H | H | H | H | H | 4-Cl—Bz | Cl | — | 77 |
| 175 | Me | H | H | H | H | H | 4-Me—Bz | Cl | — | 85 |
| 176 | Me | 2-MeO | 4-MeO | 5-Cl | H | H | H | Cl | HBr | 262 |
| 177 | Me | 2-Me | 4-MeO | 5-Cl | H | Prop | Prop | Cl | HBr | 208 |
| 178 | Me | H | H | H | H | H | 4-MeO—Bz | Cl | — | 68 |
| 179 | Me | H | H | H | H | Me | But | Cl | — | 119 |
| 180 | Me | H | H | H | H | Prop | Prop | Cl | — | 146 |
| 181 | Me | 3-NMe$_2$ | H | H | H | H | H | Cl | HBr | 169 |
| 182 | Me | 2-Me | H | H | H | Me | Me | Cl | HBr | 249 |
| 183 | Me | 4-Cl | H | H | H | Me | Me | Cl | HBr | 233 |
| 184 | Me | 2-Me | 3-Me | H | H | Me | Me | Cl | HBr | 245 |
| 185 | Me | 2-Cl | H | H | H | Et | Et | Cl | HBr | 206 |
| 186 | Me | 2-Me | H | H | H | Et | Et | Cl | HBr | 248 |
| 187 | Me | 2-Me | H | H | H | Me | But | Cl | HBr | — (amorphous, oil) |
| 188 | Me | 2-Me | 4-Me | H | H | H | H | Cl | HBr | 220 |
| 189 | Me | 2-Me | 4-Me | H | H | Prop | Prop | Cl | HBr | 236 |
| 190 | Me | 2-EtO | 5-Me | H | H | H | H | Cl | HBr | 169 |
| 191 | Me | 2-MeO | 4-Me | 5-Me | H | H | H | Cl | HBr | 255 |
| 192 | Me | 2-Me | H | H | H | Prop | Prop | Cl | HBr | 216 |
| 193 | Me | H | H | H | H | H | Prop | Cl | — | 90 |
| 194 | Me | H | H | H | H | H | 3-Me—Pent | Cl | — | 152 |
| 195 | Me | H | H | H | H | —CH$_2$—CH(Me)—CH$_2$—CH$_2$—CH(Me)— | | Cl | — | amorphous |
| 196 | Me | 4-NEt$_2$ | H | H | H | H | H | Cl | HCl | 180 |
| 197 | Me | H | H | H | H | Et | Et | Cl | — | 145 |
| 198 | sec.-But | H | H | H | H | Me | Me | Cl | HBr | 203 |
| 199 | Hex | H | H | H | H | Me | Me | Cl | HBr | 231 |
| 200 | c-Prop | H | H | H | H | Me | Me | Cl | HBr | 264 |
| 201 | c-Hex | H | H | H | H | Me | Me | Cl | HBr | 233 |

TABLE 4-continued (Legend: Me = methyl, Et = ethyl, Prop = propyl, But = butyl, Pent = pentyl, Hex = hexyl, Bz = benzyl, i = iso, sec. = secondary, c = cyclo. The substituent Y is in the 4-position on the phenyl radical, the thiazole ring being taken as in the 1-position and the sulfamoyl radical as in the 3-position)

| Example No. | $R^1$ | $R^2$ | $R^3$ | $R^4$ | $R^5$ | $R^6$ | $R^7$ | Y | HA | Melting point[*1] °C. |
|---|---|---|---|---|---|---|---|---|---|---|
| 202 | Me | 3-MeO | 4-MeO | 5-MeO | H | Me | Me | Cl | HBr | 242 |
| 203 | Prop | H | H | H | H | Me | Me | Cl | HBr | 125 |
| 204 | Me | 4-CF$_3$ | H | H | H | Me | Me | Cl | HBr | 223 |
| 205 | Me | 2-Cl | 4-Cl | 5-Me | H | Me | Me | Cl | HBr | 242 |
| 206 | Me | 3,4-O—CH$_2$—O | | H | H | Me | Me | Cl | HBr | 234 |
| 207 | Me | 3,4-O>(CH$_2$)$_2$—O | | H | H | Me | Me | Cl | HBr | 261 |
| 208 | Me | 3-MeO | 4-MeO | 5-MeO | H | H | H | Cl | HBr | 240 |
| 209 | Me | 3,4-O>CH$_2$—O | | H | H | H | H | Cl | HBr | 283 |
| 210 | Me | 3,4-O>(CH$_2$)$_2$—O | | H | H | H | H | Cl | HBr | 275 |
| 211 | Me | 3-CF$_3$ | H | H | H | H | H | Cl | HBr | 234 |
| 212 | Me | 3-CF$_3$ | H | H | H | H | H | Cl | — | 174 |
| 213 | Me | 3-CF$_3$ | H | H | H | H | H | Cl | HCl | 208 |
| 214 | Me | 4-Me | H | H | H | H | H | Cl | HCl | 184 |
| 215 | Me | 4-Me | H | H | H | H | H | Cl | HBr | 256 |
| 216 | Me | 4-EtO | H | H | H | H | H | Cl | HBr | 176 |
| 217 | Me | 4-MeO | H | H | H | Me | Me | Cl | HBr | 232 |
| 218 | Me | 2-Me | 3-Me | H | H | H | H | Cl | HCl | 189 |
| 219 | Me | 2-Et | H | H | H | H | H | Cl | HCl | 170 |
| 220 | Me | 2-Et | H | H | H | H | H | Cl | — | 124 |
| 221 | Me | 2-Et | H | H | H | H | H | Cl | HBr | 177 |
| 222 | Me | 4-MeO | H | H | H | H | H | Cl | HBr | 162 |
| 223 | Me | 4-MeO | H | H | H | H | H | Cl | HCl | 179 |
| 224 | Me | 2-Me | 4-MeO | H | H | H | H | Cl | HCl | 191 |
| 225 | Et | 4-Me | H | H | H | H | H | Cl | HBr | 212 |
| 226 | Me | H | H | H | H | Me | Me | Cl | HBr | 250 |
| 227 | Me | H | H | H | H | Me | Me | Cl | — | 138 |
| 228 | Me | 2-Cl | H | H | H | H | H | Cl | HBr | 247 |
| 229 | Me | H | H | H | H | Prop | Prop | Cl | HBr | 201 |
| 230 | Me | H | H | H | H | Prop | Prop | Cl | — | 117 |
| 231 | Me | 2-Cl | H | H | H | Prop | Prop | Cl | HBr | 227 |
| 232 | Me | 2-Cl | H | H | H | Prop | Prop | Cl | — | 126 |
| 233 | Me | 4-Cl | H | H | H | H | H | Cl | HBr | 168 |
| 234 | Me | 4-Cl | H | H | H | H | H | Cl | — | 228 |
| 235 | Me | 4-NEt$_2$ | H | H | H | H | H | Cl | HBr | 172 |
| 236 | Me | 4-NEt$_2$ | H | H | H | H | H | Cl | — | 179 |
| 237 | Me | 2-Me | 3-Me | H | H | H | Me | Cl | — | 100 |
| 238 | Me | H | H | H | H | —(CH$_2$)$_5$— | | Cl | — | 110 |
| 239 | Me | H | H | H | H | —(CH$_2$)$_4$— | | Cl | — | 110 |
| 240 | Me | H | H | H | H | H | dodecyl | Cl | — | — (oil) |
| 241 | Me | H | H | H | H | But | H | Cl | — | 120 |
| 242 | Me | H | H | H | H | H | Hex | Cl | — | — (oil) |
| 243 | Me | 2-Me | 3-Me | H | H | H | H | Cl | HBr | 189 |
| 244 | Me | 2-Me | 3-Me | H | H | H | H | Cl | — | 110 |
| 245 | Me | 2-Me | 3-Me | H | H | H | Me | Cl | HBr | 237 |
| 246 | Me | 2-Me | H | H | H | H | sec.-But | Cl | HBr | 252 |
| 247 | Me | 3-Cl | H | H | H | H | H | Cl | HCl | 205 |
| 248 | Me | 4-i-Prop | H | H | H | H | H | Cl | HCl | 270 |
| 249 | Me | 2-Cl | H | H | H | H | H | Cl | HCl | 186 |
| 250 | Me | 2-MeO | H | H | H | H | H | Cl | HCl | 247 |
| 251 | Me | 4-EtO | H | H | H | H | H | Cl | HCl | 174 |
| 252 | Me | 2-MeO | Cl | H | H | H | H | Cl | HCl | 209 |
| 253 | Me | 3-CF$_3$ | H | H | H | H | H | Br | HBr | 215 |
| 254 | Me | 3-CF$_3$ | H | H | H | H | H | Br | — | 94 |
| 255 | Et | H | H | H | H | H | H | Cl | HBr | 249 |
| 256 | Et | H | H | H | H | H | H | Cl | — | 155 |
| 257 | Me | H | H | H | H | H | H | Cl | HCl | 179 |
| 258 | Me | H | H | H | H | H | H | Cl | — | 126 |
| 259 | Me | H | H | H | H | H | H | Br | HBr | 162 |
| 260 | Me | H | H | H | Me | H | H | Cl | HBr | 145 |
| 261 | Me | H | H | H | Et | H | H | Cl | HBr | 144 |
| 262 | Me | H | H | H | H | H | c-Pent | Cl | — | 94 |
| 263 | Me | H | H | H | H | H | c-Hex | Cl | — | 108 |
| 264 | Me | H | H | H | H | H | c-Hex | Cl | HCl | |
| 265 | Me | H | H | H | H | H | Allyl | Cl | — | 87 |

TABLE 4-continued (Legend: Me = methyl, Et = ethyl, Prop = propyl, But = butyl, Pent = pentyl,
Hex = hexyl, Bz = benzyl, i = iso, sec. = secondary, c = cyclo. The substituent
Y is in the 4-position on the phenyl radical, the thiazole ring being taken as in
the 1-position and the sulfamoyl radical as in the 3-position)

| Example No. | $R^1$ | $R^2$ | $R^3$ | $R^4$ | $R^5$ | $R^6$ | $R^7$ | Y | HA | Melting point*[1] °C. |
|---|---|---|---|---|---|---|---|---|---|---|
| 266 | Me | H | H | H | H | Me | c-Hex | Cl | — | 143 |
| 267 | Me | H | H | H | H | H | Bz | Cl | — | 73 |
| 268 | Me | H | H | H | H | Me | Bz | Cl | — | 69 |
| 269 | Me | H | H | H | H | H | 2,4-(MeO)$_2$—Bz | Cl | — | 74 |
| 270 | Me | H | H | H | H | H | 2-Cl—Bz | Cl | — | 77 |
| 271 | Me | 4-MeO | H | H | H | H | H | Br | HBr | 177 |
| 272 | Me | 4-MeO | H | H | H | Prop | Prop | Cl | HBr | 206 |
| 273 | Prop | H | H | H | H | H | H | Cl | HBr | 149 |
| 274 | Allyl | H | H | H | H | H | H | Cl | HBr | 242 |
| 275 | sec.-But | H | H | H | H | H | H | Cl | HBr | 260 |
| 276 | Me | 4-MeO | H | H | H | Me | Me | Cl | HBr | 214 |
| 277 | Me | H | H | H | H | H | c-Pent | Cl | HCl | 164 |
| 278 | Me | 4-EtO | H | H | H | H | H | Cl | HBr | 176 |
| 279 | Me | 4-Br | H | H | H | Me | Me | Cl | HBr | 269 |
| 280 | Me | 2-Me | H | 6-Me | H | Me | Me | Cl | HBr | 244 |
| 281 | Me | 2-Br | H | H | H | Me | Me | Cl | HBr | 242 |

*[1]Most of the compounds listed melt with decomposition.

EXAMPLE 282

4-(4-Chloro-3-dimethylsulfamoylphenyl)-3-methyl-2-phenylimino-4-thiazoline (a) 3-Methyl-4-oxo-2-phenyliminothiazolidine hydrobromide 10 g of ethyl bromoacetate and 9.95 g of 1-methyl-3-phenylthiourea in 150 ml of acetone are boiled for 1 hour under a reflux condenser. The reaction mixture is allowed to cool and the crystals are filtered off and washed with acetone. Melting point 212°–215° C.

(b) 3-Methyl-4-oxo-2-phenyliminothiazolidine 4 g of 3-methyl-4-oxo-2-phenyliminothiazolidine hydrobromide are suspended in 100 ml of ethanol and 8.4 g of triethylamine are added. The resulting solution is stirred for 3 hours at room temperature, the ethanol is distilled off, water is added to the residue, the mixture is extracted several times with ethyl acetate and, after drying the organic phases over sodium sulfate, the solvent is distilled off. Yellow viscous oil.

(c) 4-(4-Chloro-3-dimethylsulfamoylphenyl)-3-methyl-2-phenylimino-4-thiazoline 20 mmoles of tert.-butyl-lithium in pentane are added in the course of 10 minutes to a solution of 3 g of 5-bromo-2-chlorobenzene-dimethylsulfonamide in 40 ml of absolute tetrahydrofuran, this solution being stirred at −78° C. under argon. The solution is kept at −78° C. for about 60 minutes, 2 g of 3-methyl-4-oxo-2-phenyliminothiazoline are then added and the reaction mixture is stirred overnight at room temperature. It is poured into 15 ml of saturated ammonium chloride solution, the resulting solution is extracted several times with chloroform and the combined organic phases are washed with water and dried over magnesium sulfate. After filtering off the desiccant, 60 ml of glacial acetic acid are added, the mixture is heated at the boil for 2 hours, the solvent is distilled off and, after dissolving the residue in 5 ml of chloroform, the resulting solution is subjected to chromatography on a silica gel column using a 1:1 mixture of ethyl acetate/toluene. Crystals with a melting point of 177°–179° C.

EXAMPLE 283

4-(4-Chloro-3-dimethylsulfamoylphenyl)-3-methyl-2-phenylimino-4-thiazoline (a) N-Methyl-N'-phenylcarbodiimide A suspension of 2.05 g of N-methyl-N'-phenyl-chloroformamidine hydrochloride in 8 ml of chloroform is added, at 10°–12° C., to 6 g of 20% strength sodium hydroxide solution. The mixture is stirred for 10 minutes, the organic phase is separated off, the aqueous phase is extracted twice more with chloroform and the combined organic phases are dried over K$_2$CO$_3$. After filtering off the desiccant, the solution is subjected to further reaction without isolating the carbodiimide.

(b) 4-(4-Chloro-3-dimethylsulfamoylphenyl)-3-methyl-2-phenylimino-4-thiazoline

The solution prepared under (a) is added to a solution of 2.8 g of 4'-chloro-3'-dimethylsulfamoylacetophenone-2-thiol in 55 ml of chloroform, the latter solution being stirred with the exclusion of oxygen, and the resulting mixture is stirred for 2 hours at room temperature and boiled for a further 4 hours under a reflux condenser. After distilling off the chloroform, the residue is boiled for 30 minutes in 25 ml of glacial acetic acid, the solvent is distilled off and the residue is subjected—as described in Example 282c—to column chromatography on silica gel using 1:1 ethyl acetate/toluene as the eluant. Pale yellow crystals with a melting point of 177°–180° C.

EXAMPLE 284

4-(4-Chloro-3-dimethylsulfamoylphenyl)-3-methyl-2-phenylimino-4-thiazoline (a) N-Methyl-N'-phenyl-chloroformamidine hydrochloride After passing 6.3 g of phosgene into 40 ml of absolute tetrahydrofuran at room temperature, 8 g of 1-methyl-3-phenylthiourea are added, with stirring, the color of the suspension changing instantaneously to yellow. After adding 0.5 ml of dimethylformamide, the mixture is stirred for 20 hours at room temperature, nitrogen is then passed through the reaction mixture for about 30 minutes, in order to drive off the phosgene, and the crystals are filtered off and washed with tetrahydrofuran. Crystals with a melting point of 169° C. (with decomposition).

(b)
4-(4-Chloro-3-dimethylsulfamoylphenyl)-3-methyl-2-phenylimino-4-thiazoline

A solution of 2 g of triethylamine in 10 ml of isopropanol is added dropwise in the course of 30 minutes to a mixture of 3 g of 4'-chloro-3'-dimethylsulfamoylacetophenone-2-thiol and 2.1 g of N-methyl-N'-phenylchloroformamidine hydrochloride in 50 ml of isopropanol, with the exclusion of moisture and with external cooling, the reaction temperature being kept between 10° and 15° C. during the addition.

After adding 50 ml of chloroform, the mixture is stirred overnight at room temperature and after adding 20 ml of glacial acetic acid it is boiled for 1 hour under a reflux condenser. The solvent is distilled off under reduced pressure, the residue is taken up in 10 ml of chloroform and the organic phase is washed with water and, after drying over MgSO4, is subjected to column chromatography (silica gel, eluant: 1:1 ethyl acetate/toluene). Colorless crystals with a melting point of 178°–180° C. (from ethanol/ethyl acetate).

EXAMPLE 285

4-(4-Chloro-3-sulfamoylphenyl)-3-methyl-2-phenylimino-4-thiazolidine (a) 2-Bromo-1-(4-chloro-3-sulfamoylphenyl)-ethanol 0.94 g of sodium cyanoborohydride are added to an ice-cold solution of 3.1 g of 2-bromo-4'-chloro-3'-sulfamoylacetophenone and 1 ml of aqueous methyl orange solution in 20 ml of tetrahydrofuran, with stirring, and the pH is then rapidly adjusted to 3-4 by the dropwise addition of a 1:1 mixture of glacial acetic acid and 2 N HCl (indicator red in color) and the pH is then kept at this value by the occasional dropwise addition of the acid mixture. After about 1½ hours no further starting material can be detected in a thin layer chromatogram (Merck silica gel ready-for-use plates, ethyl acetate as the solvent). The reaction mixture is poured into 300 ml of water and the resulting mixture is saturated with sodium chloride and extracted several times with ethyl acetate. After the combined organic phases have been washed with water and dried over sodium sulfate, they are concentrated in a rotary evaporator. Colorless crystals with a melting point of 145° C. (with decomposition).

(b)
S-[2-(4-Chloro-3-sulfamoylphenyl)-2-hydroxyethyl]-N-methyl-N'-phenylisothioronium bromide 1.6 g of 2-bromo-1-(4-chloro-3-sulfamoylphenyl)ethanol are added to a solution of 0.8 g of 1-methyl-3-phenyl-thiourea in 30 ml of acetone. After stirring at room temperature for 48 hours, the solvent is distilled off under reduced pressure and the residue is crystallized under diisopropyl ether. Yellow solid with a melting point of 115° C. (with decomposition).

(c)
4-(4-Chloro-3-sulfamoylphenyl)-3-methyl-2-phenylimino-4-thiazoline 1.5 g of s-[2-(4-chloro-3-sulfamoylphenyl)-2-hydroxyethyl]-N-methyl-N'-phenylisothioronium bromide are dissolved in 70 ml of methylene chloride and, after adding 15 g of active manganese-IV oxide, the mixture is stirred at room temperature for 30 hours. After filtering off the inorganic precipitate, the organic phase is stirred vigorously for 1 hour with aqueous sodium bicarbonate solution and washed once with water, 50 ml of glacial acetic acid are added, the resulting mixture is boiled for 1 hour under a reflux condenser and the solvent is driven off under reduced pressure. The residue has a thin layer chromatogram identical to that of the product of Example 73 (Merck silica gel ready-for-use plates; solvent: ethyl acetate) and a melting point of 168°–171° C.

EXAMPLE 286

4-(4-Chloro-3-N-methyl-N-cyclohexylsulfamoylphenyl)-3-methyl-2-phenylimino-4-thiazoline Obtained by a procedure analogous to that indicated in Example 138, using N-methyl-N-cyclohexylamine as the amine component. Colorless crystals with a melting point of 180°–181° C.

EXAMPLE 287

4-[4-Chloro-3-(1-methyl-4-piperazinylsulfonyl)-phenyl]-3-methyl-2-phenylimino-4-thiazoline Obtained by a procedure analogous to that indicated in Example 138, using N-methylpiperazine as the amine component. Colorless crystals with a melting point of 160° C. (with decomposition).

The thiazolines of the formula I listed in the following examples are obtained from the correspondingly substituted ketones of the formula II in which X denotes chlorine or bromine and Z denotes $NR^6R^7$, by a procedure analogous to that indicated in Example 1(a):

EXAMPLE 288

4-(4-Fluoro-3-sulfamoylphenyl)-3-methyl-2-phenylimino-4-thiazoline hydrobromide, melting point 281° C. (with decomposition).

EXAMPLE 289

3-Methyl-4-(4-methyl-3-sulfamoylphenyl)-2-phenylimino-4-thiazoline hydrochloride, melting point 268° C. (with decomposition).

EXAMPLE 290

3-Methyl-4-(3-dimethylsulfamoylphenyl)-2-phenylimino-4-thiazoline hydrobromide, melting point 254° C. (with decomposition).

EXAMPLE 291

2-(4-Methoxyphenyl-imino)-3-methyl-4-(3-dimethylsulfamoylphenyl)-4-thiazoline hydrobromide, melting point 234° C. (with decomposition).

EXAMPLE 292

4-(4-Chloro-3-dimethylsulfamoylphenyl)-2-(3-trifluoromethylphenyl-imino)-3-methyl-4-thiazoline hydrobromide, melting point 242° C.

EXAMPLE 293

4-(4-Chloro-3-methylsulfamoylphenyl)-3-methyl-2-phenylimino-4-thiazoline hydrobromide, melting point 269° C.

EXAMPLE 294

3-Allyl-4-(4-chloro-3-dimethylsulfamoylphenyl)-2-phenylimino-4-thiazoline hydrobromide, melting point 207° C. (with decomposition).

EXAMPLE 295

4-(4-Chloro-3-sulfamoylphenyl)-3-cyclopentyl-2-phenylimino-4-thiazoline hydrobromide, melting point 236° C.

EXAMPLE 296

4-(4-Chloro-3-sulfamoylphenyl)-3-cyclooctyl-2-phenylimino-4-thiazoline hydrobromide, melting point 217° C.

EXAMPLE 297

3-Methyl-4-(4-methyl-3-dimethylsulfamoylphenyl)-2-phenylimino-4-thiazoline hydrobromide, melting point 226° C.

EXAMPLE 298

2-(4-Methoxyphenyl-imino)-3-methyl-4-(4-methyl-3-dimethylsulfamoylphenyl)-4-thiazoline hydrobromide, melting point 186° C.

EXAMPLE 299

2-(2-Chlorophenyl-imino)-3-methyl-4-(4-methyl-3-dimethylsulfamoylphenyl)-4-thiazoline hydrobromide, melting point 218° C.

EXAMPLE 300

3-Ethyl-4-(4-methyl-3-dimethylsulfamoylphenyl)-2-phenylimino-4-thiazoline hydrobromide, melting point 225° C.

The basic compounds of the formula I listed in the following examples can be obtained from the acid addition salts of the compounds of the formula I by the action of a base, by procedures analogous to those indicated in Examples 2(a), 27 and 35(b):

EXAMPLE 301

3-Methyl-4-(3-dimethylsulfamoylphenyl)-2-phenylimino-4-thiazoline, melting point 254° C.

EXAMPLE 302

2-(4-Methoxyphenylimino)-3-methyl-4-(3-dimethylsulfamoylphenyl)-4-thiazoline, melting point 234° C.

EXAMPLE 303

4-(4-Chloro-3-dimethylsulfamoylphenyl)-3-methyl-2-(3-trifluoromethylphenyl-imino)-4-thiazoline, melting point 226° C.

EXAMPLE 304

4-(4-Chloro-3-methylsulfamoylphenyl)-3-methyl-2-phenylimino-4-thiazoline, melting point 274° C.

EXAMPLE 305

2-(4-Bromophenylimino)-4-(4-chloro-3-dimethylsulfamoylphenyl)-3-methyl-4-thiazoline, melting point 185°–188° C.

EXAMPLE 306

2-(2-Bromophenylimino)-4-(4-chloro-3-dimethylsulfamoylphenyl)-3-methyl-4-thiazoline, melting point 155° C.

EXAMPLE 307

3-Methyl-4-(4-methyl-3-dimethylsulfamoylphenyl)-2-phenylimino-4-thiazoline, melting point 175° C.

EXAMPLE 308

2-(4-Methoxyphenyl-imino)-3-methyl-4-(4-methyl-3-dimethylsulfamoylphenyl)-4-thiazoline, melting point 180° C.

EXAMPLE 309

2-(4-Chlorophenyl-imino)-3-methyl-4-(4-methyl-3-dimethylsulfamoylphenyl)-4-thiazoline, melting point 172° C.

EXAMPLE 310

3-Ethyl-4-(4-methyl-3-dimethylsulfamoylphenyl)-2-phenylimino-4-thiazoline, melting point 175° C.

EXAMPLE 311

4-(4-Chloro-3-dimethylsulfamoylphenyl)-3-methyl-2-(2,6-dimethylphenyl-imino)-4-thiazoline, melting point 180° C.

The thiazoline derivatives of the formula I listed in the following examples are obtained from the correspondingly substituted thiazolidin-4-ol derivatives IV, by a procedure analogous to that indicated in Example 1(b):

EXAMPLE 312

4-(4-Chloro-3-dimethylsulfamoylphenyl)-3-methyl-2-(2,6-dimethylphenylimino)-4-thiazoline hydrobromide, melting point 249° C.

EXAMPLE 313

2-(2-Bromophenylimino)-4-(4-chloro-3-dimethylsulfamoylphenyl)-3-methyl-4-thiazoline hydrobromide, melting point 245° C.

EXAMPLE 314

2-(4-Bromophenylimino)-4-(4-chloro-3-dimethylsulfamoylphenyl)-3-methyl-4-thiazoline hydrobromide, melting point 269° C.

EXAMPLE 315

3-Methyl-4-(2-methyl-5-dimethylsulfamoylphenyl)-2-phenylimino-4-thiazoline hydrobromide, melting point 236° C. (with decomposition).

EXAMPLE 316

3-Methyl-4-(3-methyl-5-dimethylsulfamoylphenyl)-2-phenylimino-4-thiazoline hydrobromide, melting point 205° C. (with decomposition).

EXAMPLE 317

2-(2-Chlorophenylimino)-3-methyl-4-(2-methyl-5-dimethylsulfamoylphenyl)-4-thiazoline hydrobromide, melting point 234° C. (with decomposition).

EXAMPLE 318

2-(4-Methoxyphenylimino)-3-methyl-4-(3-methyl-5-dimethylsulfamoylphenyl)-4-thiazoline hydrobromide, melting point 247° C. (with decomposition).

EXAMPLE 319

2-(4-Isopropylphenyl-imino)-3-methyl-4-(3-methyl-5-dimethylsulfamoylphenyl)-4-thiazoline hydrobromide, melting point 224° C. (with decomposition).

EXAMPLE 320

2-(4-Chlorophenyl-imino)-3-methyl-4-(3-methyl-5-dimethylsulfamoylphenyl)-4-thiazoline hydrobromide, melting point 212° C. (with decomposition).

EXAMPLE 321

2-(4-Fluorophenyl-imino)-3-methyl-4-(2-methyl-5-dimethylsulfamoylphenyl)-4-thiazoline hydrobromide, melting point 225° C. (with decomposition).

EXAMPLE 322

3-Methyl-2-(2-methylphenyl-imino)-4-(2-methyl-5-dimethylsulfamoylphenyl)-4-thiazoline hydrobromide, melting point 263° C. (with decomposition).

EXAMPLE 323

2-(4-Fluorophenyl-imino)-3-methyl-4-(3-methyl-5-dimethylsulfamoylphenyl)-4-thiazoline hydrobromide, melting point 222° C. (with decomposition).

EXAMPLE 324

3-Methyl-2-(2-methylphenyl-imino)-4-(3-methyl-5-dimethylsulfamoylphenyl)-4-thiazoline hydrobromide, melting point 207° C. (with decomposition).

EXAMPLE 325

2-(2-Chlorophenyl-imino)-4-(2-chloro-5-dimethylsulfamoylphenyl)-3-methyl-4-thiazoline hydrobromide, melting point 227° C. (with decomposition).

EXAMPLE 326

2-(2-Chlorophenylimino)-4-(3-chloro-5-dimethylsulfamoylphenyl)-3-methyl-4-thiazoline hydrobromide, melting point 242° C. (with decomposition).

EXAMPLE 327

4-(3-Chloro-5-dimethylsulfamoylphenyl)-2-(4-methoxyphenyl-imino)-3-methyl-4-thiazoline hydrobromide, melting point 228° C. (with decomposition).

EXAMPLE 328

3-Ethyl-4-(3-chloro-5-dimethylsulfamoylphenyl)-2-phenylimino-4-thiazoline hydrobromide, melting point 230° C. (with decomposition).

EXAMPLE 329

3-Methyl-4-(2-methyl-5-sulfamoylphenyl)-2-phenylimino-4-thiazoline hydrobromide, melting point 220° C. (with decomposition).

EXAMPLE 330

2-(2-Chlorophenyl-imino)-3-methyl-4-(2-methyl-5-sulfamoylphenyl)-4-thiazoline hydrobromide, melting point 195° C. (with decomposition).

EXAMPLE 331

3-Methyl-4-(3-methyl-5-sulfamoylphenyl)-2-phenylimino-4-thiazoline hydrobromide, melting point 280° C. (with decomposition).

EXAMPLE 332

2-(4-Chlorophenyl-imino)-3-methyl-4-(3-methyl-5-sulfamoyl-phenyl)-4-thiazoline hydrobromide, melting point 257° C. (with decomposition).

EXAMPLE 333

2-(4-Isopropylphenyl-imino)-3-methyl-4-(3-methyl-5-sulfamoylphenyl)-4-thiazoline hydrobromide, melting point 256° C. (with decomposition).

EXAMPLE 334

2-(4-Methoxyphenyl-imino)-3-methyl-4-(2-methyl-5-sulfamoylphenyl)-4-thiazoline hydrobromide, melting point 170° C. (with decomposition).

EXAMPLE 335

4-(2-Chloro-5-dimethylsulfamoylphenyl)-2-(4-methoxyphenyl-imino)-3-methyl-4-thiazoline hydrobromide, melting point 249° C.

EXAMPLE 336

4-(2-Chloro-5-dimethylsulfamoylphenyl)-3-methyl-2-(4-methylphenyl-imino)-4-thiazoline hydrobromide, melting point 205° C.

EXAMPLE 337

4-(2Chloro-5-sulfamoylphenyl)-3-methyl-2-phenylimino-4-thiazoline hydrobromide, melting point 276° C. (with decomposition).

EXAMPLE 338

2-(2-Chlorophenyl-imino)-4-(2-chloro-5-sulfamoylphenyl)-3-methyl-4-thiazoline hydrobromide, melting point 254° C. (with decomposition).

EXAMPLE 339

3-Ethyl-4-(2-chloro-5-sulfamoylphenyl)-2-phenylimino-4-thiazoline hydrobromide, melting point 257° C. (with decomposition).

EXAMPLE 340

4-(2-Chloro-5-sulfamoylphenyl)-2-(3-trifluoromethyl-phenyl-imino)-3-methyl-4-thiazoline hydrobromide, melting point 268° C.

EXAMPLE 341

4-(2-Chloro-5-sulfamoylphenyl)-2-(4-methoxyphenyl-imino)-3-methyl-4-thiazoline hydrobromide, melting point 267° C. (with decomposition).

EXAMPLE 342

4-(2-Chloro-5-methylsulfamoylphenyl)-3-methyl-2-phenylimino-4-thiazoline hydrobromide, melting point 270° C. (with decomposition).

EXAMPLE 343

2-(2-Chlorophenyl-imino)-4-(2-chloro-5-methylsulfamoylphenyl)-3-methyl-4-thiazoline hydrobromide, melting point 257° C. (with decomposition).

EXAMPLE 344

3-Ethyl-4-(2-chloro-5-methylsulfamoylphenyl)-2-phenylimino-4-thiazoline hydrobromide, melting point 236° C. (with decomposition).

EXAMPLE 345

4-(2-Chloro-5-methylsulfamoylphenyl)-2-(3-trifluoromethylphenyl-imino)-3-methyl-4-thiazoline hydrobromide, melting point 208° C. (with decomposition).

EXAMPLE 346

4-(2-Chloro-5-methylsulfamoylphenyl)-2-(4-methoxyphenylimino)-3-methyl-4-thiazoline hydrobromide, melting point 257° C. (with decomposition).

EXAMPLE 347

4-(2-Bromo-5-dimethylsulfamoylphenyl)-3-methyl-2-phenylimino-4-thiazoline hydrobromide, melting point 225°–227° C. (with decomposition).

EXAMPLE 348

4-(2-Bromo-5-dimethylsulfamoylphenyl)-2-(2-chlorophenylimino)-3-methyl-4-thiazoline hydrobromide, melting point 227° C.

EXAMPLE 349

4-(2-Bromo-5-dimethylsulfamoylphenyl)-3-methyl-2-(2,4-dimethylphenyl-imino)-4-thiazoline hydrobromide, melting point 227°–228° C. (with decomposition).

EXAMPLE 350

4-Ethyl-4-(2-bromo-5-dimethylsulfamoylphenyl)-2-(2-methylphenylimino)-4-thiazoline hydrobromide, melting point 205°–208° C. (with decomposition).

The basic compounds of the formula I listed in the following examples can be obtained from the corresponding acid addition salts of the compounds of the formula I by the action of a base, by procedures analogous to those indicated in Examples 2(a), 27 and 35(b):

EXAMPLE 351

3-Methyl-4-(2-methyl-5-dimethylsulfamoylphenyl)-2-phenylimino-4-thiazoline, melting point 190° C.

EXAMPLE 352

3-Methyl-4-(3-methyl-5-dimethylsulfamoylphenyl)-2-phenylimino-4-thiazoline, melting point 166° C.

EXAMPLE 353

4-(2-Chloro-5-dimethylsulfamoylphenyl)-3-methyl-2-phenylimino-4-thiazoline, melting point 197° C.

EXAMPLE 354

4-(3-Chloro-5-dimethylsulfamoylphenyl)-3-methyl-2-phenylimino-4-thiazoline, melting point 167° C.

EXAMPLE 355

4-(2-Chloro-5-dimethylsulfamoylphenyl)-2-(2-chlorophenylimino)-3-methyl-4-thiazoline, melting point 227° C.

EXAMPLE 356

3-Ethyl-4-(2-chloro-5-dimethylsulfamoylphenyl)-2-phenylimino-4-thiazoline, melting point 201° C. (with decomposition).

EXAMPLE 357

4-(3-Chloro-5-dimethylsulfamoylphenyl)-2-(2-chlorophenylimino)-3-methyl-4-thiazoline, melting point 163° C.

EXAMPLE 358

3-Methyl-4-(2-methyl-5-sulfamoylphenyl)-2-phenylimino-4-thiazoline, melting point 188°–191° C.

EXAMPLE 359

3-Methyl-4-(3-methyl-5-sulfamoylphenyl)-2-phenylimino-4-thiazoline, melting point 210°–212° C.

EXAMPLE 360

4-(2-Chloro-5-sulfamoylphenyl)-3-methyl-2-phenylimino-4-thiazoline, melting point 198°–200° C.

EXAMPLE 361

4-(2-Bromo-5-dimethylsulfamoylphenyl)-3-methyl-2phenylimino-4-thiazoline, melting point 204° C.

EXAMPLE 362

4-(2-Bromo-5-dimethylsulfamoylphenyl)-3-methyl-2-(2-chlorophenylimino)-4-thiazoline, melting point 242° C. (with decomposition).

EXAMPLE 363

4-(2-Bromo-5-dimethylsulfamoylphenyl)-3-methyl-2-(2,4-dimethylphenyl-imino)-4-thiazoline, melting point 260° C. (with decomposition).

EXAMPLE 364

3-Ethyl-4-(2-bromo-5-dimethylsulfamoylphenyl)-2-(2-methylphenyl-imino)-4-thiazoline, melting point 209°–210° C. (with decomposition).

EXAMPLE 365

2-(4-Methoxyphenyl-imino)-3-methyl-4-(2-methyl-5-dimethylsulfamoylphenyl)-4-thiazoline, melting point 186°–189° C.

EXAMPLE 366

3-Ethyl-4-(3-methyl-5-dimethylsulfamoylphenyl)-2-(2-methylphenylimino)-4-thiazoline, melting point 155° C.

EXAMPLE 367

2-(4-Chlorophenyl-imino)-3-methyl-4-(3-methyl-5-sulfamoylphenyl)-4-thiazoline, melting point 195° C.

The thiazolines of the formula I listed in the following examples are obtained from the correspondingly substituted ketones of the formula II in which X denotes bromine and Z denotes $NR^6R^7$, by a procedure corresponding to that indicated in Example 1(a):

EXAMPLE 368

4-(2-Chloro-5-dimethylsulfamoylphenyl)-3-methyl-2-phenylimino-4-thiazoline hydrobromide, melting point 247° C. (with decomposition).

EXAMPLE 369

4-(3-Chloro-5-dimethylsulfamoylphenyl)-3-methyl-2-phenylimino-4-thiazoline hydrobromide, melting point 234° C. (with decomposition).

EXAMPLE 370

3-Ethyl-4-(2-chloro-5-dimethylsulfamoylphenyl)-2-phenylimino-4-thiazoline hydrobromide, melting point 175° C. (with decomposition).

EXAMPLE 371

4-(2-Chloro-5-dimethylsulfamoylphenyl)-2-(2-chloro-phenylimino)-3-methyl-4-thiazoline hydrobromide, melting point 227° C. (with decomposition).

EXAMPLE 372

4-(2-Chloro-5-dimethylsulfamoylphenyl)-3-methyl-2-phenylimino-4-thiazoline with a melting point of 195°-197° C. is obtained by a procedure analogous to that indicated in Example 284(b), by reacting 2'-chloro-5'-dimethylsulfamoylacetophenone-2-thiol with N-methyl-N'-phenyl-chloroformamidine hydrochloride.

The 2'-chloro-5'-dimethylsulfamoylacetophenone-2-thiol used is obtained in the form of a pale yellow crystalline powder by alkaline hydrolysis of 2-acetylthio-2'-chloro-5'-dimethylsulfamoylacetophenone with 5% strength aqueous sodium hydroxide solution at room temperature, under an argon atmosphere as the blanketing gas.

2-Acetylthio-2'-chloro-5'-dimethylsulfamoylacetophenone is obtained by reacting 2-bromo-2'-chloro-5'-dimethylsulfamoylacetophenone with thioacetic acid, which has been neutralized with KOH, in ethanol. After the reaction, the reaction mixture is poured into water, the resulting mixture is extracted with ethyl acetate, the organic phase is dried over magnesium sulfate and the residue obtained by evaporation of the solvent is recrystallized from isopropanol (active charcoal). Melting point 84°-88° C.

The compounds of the formula IV listed in Table 4(a) which follows are also obtained by a procedure analogous to that of Example 155:

TABLE 4(a)

(Lenged as for Table 4; the position of the substituent Y is indicated in each case, the sulfamoyl group being taken as in the 5-position)

| Example No. | R¹ | R² | R³ | R⁴ | R⁵ | R⁶ | R⁷ | Y | HA | Melting point*¹ (°C.) |
|---|---|---|---|---|---|---|---|---|---|---|
| 373 | Me | H | H | H | H | Me | Me | 2-Me | HBr | 192 |
| 374 | Me | H | H | H | H | Me | Me | 3-Me | HBr | 205 |
| 375 | Me | 2-Cl | H | H | H | Me | Me | 2-Me | HBr | 228 |
| 376 | ME | 4-MeO | H | H | H | Me | Me | 3-Me | HBr | 157 |
| 377 | Me | 4-iProp | H | H | H | Me | Me | 3-Me | HBr | 219 |
| 378 | Me | 4-Cl | H | H | H | Me | Me | 3-Me | HBr | 212 |
| 379 | Me | 4-F | H | H | H | Me | Me | 2-Me | HBr | 220 |
| 380 | Me | 2-Me | H | H | H | Me | Me | 2-Me | HBr | 225 |
| 381 | Me | 4-F | H | H | H | Me | Me | 3-Me | HBr | 217 |
| 382 | Me | 2-Me | H | H | H | Me | Me | 3-Me | HBr | 208 |
| 383 | Me | 2-Cl | H | H | H | Me | Me | 2-Cl | HBr | 186 |
| 384 | Me | 2-Cl | H | H | H | Me | Me | 3-Cl | HBr | 237 |
| 385 | Me | 4-MeO | H | H | H | Me | Me | 3-Cl | HBr | 225 |
| 386 | Et | H | H | H | H | Me | Me | 3-Cl | HBr | 202 |
| 387 | Me | H | H | H | H | H | H | 2-Me | HBr | 208 |
| 388 | Me | 2-Cl | H | H | H | H | H | 2-Me | HBr | 180 |
| 389 | Me | H | H | H | H | H | H | 3-Me | HBr | 280 |
| 390 | Me | 4-Cl | H | H | H | H | H | 3-Me | HBr | 160 |
| 391 | Me | 4-iProp | H | H | H | H | H | 3-Me | HBr | 254 |
| 392 | Me | 4-OMe | H | H | H | H | H | 2-Me | HBr | 184 |
| 393 | Me | 4-OMe | H | H | H | Me | Me | 2-Cl | HBr | 177 |
| 394 | Me | 4-Me | H | H | H | Me | Me | 2-Cl | HBr | 197 |
| 395 | Me | H | H | H | H | H | H | 2-Cl | HBr | 271 |
| 396 | Me | 2-Cl | H | H | H | H | H | 2-Cl | HBr | 254 |
| 397 | Et | H | H | H | H | H | H | 2-Cl | HBr | 210 |
| 398 | Me | 3-CF₃ | H | H | H | H | H | 2-Cl | HBr | 268 |
| 399 | Me | 4-OMe | H | H | H | H | H | 2-Cl | HBr | 168 |
| 400 | Me | H | H | H | H | H | Me | 2-Cl | HBr | 268 |
| 401 | Me | 2-Cl | H | H | H | H | Me | 2-Cl | HBr | 190 |
| 402 | Et | H | H | H | H | H | Me | 2-Cl | HBr | 236 |
| 403 | Me | 3-CF₃ | H | H | H | H | Me | 2-Cl | HBr | 208 |
| 404 | Me | 4-OMe | H | H | H | H | Me | 2-Cl | HBr | 200 |
| 405 | Me | H | H | H | H | Me | Me | 2-Br | HBr | 239 |
| 406 | Me | 2-Cl | H | H | H | Me | Me | 2-Br | HBr | 193 |
| 407 | Me | 2-Me | 4-Me | H | H | Me | Me | 2-Br | HBr | 203 |
| 408 | Et | 2-Me | H | H | H | Me | Me | 2-Br | HBr | 188 |

Preparation of compounds of the formula II

Preparation of
2-bromo-3'-methyl-5'-sulfamoylacetophenone

About 5 ml of a solution of 3.7 g (0.0294 mole) of bromine in 30 ml of ethyl acetate is added dropwise to a suspension of 5 g (0.0234 mole) of 3'-methyl-5'-sulfamoylacetophenone in 70 ml of ethyl acetate and the mixture is warmed at about 40° C. until the bromine color suddenly disappears. The remainder of the bromine solution is now added rapidly dropwise at room temperature, with stirring, and the solvent is then distilled off. Crystals with a melting point of 188°-191° C. (from isopropanol).

The bromoacetophenones listed below were prepared in an analogous manner: 2,2'-dibromo-5'-dimethylsulfamoyl-acetophenone, melting point 88° C., 2-bromo-3'-chloro-5'-dimethylsulfamoyl-acetophenone, melting point 77°-78° C., 2-bromo-2'-chloro-5'-methylsulfamoyl-acetophenone, melting point 99°-101° C., 2-bromo-2'-chloro-5'-dimethylsulfamoyl-acetophenone, melting point 87°-88° C., 2-bromo-2'-chloro-5'-sulfamoylacetophenone, melting point 152°-154° C., 2-bromo-3'-methyl-5'-dimethylsulfamoylacetophenone, melting point 71°-75° C., 2-bromo-2'-methyl-5'-dimethylsulfamoylacetophenone, melting point 69°-71° C.

and 2-bromo-2'-methyl-5'-sulfamoylacetophenone, melting point 112°-115° C.

Preparation of 2'-methyl-5'-sulfamoylacetophenone 0.25 ml of carbon tetrachloride is added to a suspension of 2.7 g (0.11 mole) of magnesium turnings in 2.5 g (0.043 mole) of anhydrous alcohol, the temperature rising to 40° C., and 75 ml of ethanol (absolute) are then added slowly dropwise. The mixture is heated to the boil and a small portion of a solution of 17.6 g (0.11 mole) of diethyl malonate, 10 ml (0.17 mole) of absolute ethanol and 12.5 ml of diethyl ether is added. After the reaction has started, the remainder of the solution is added dropwise at a rate such that the mixture remains at the boil without external heating. The mixture is then heated for a further 3 hours under reflux, during which time the magnesium is dissolved, and a solution of 11.6 g (0.05 mole) of 2-methyl-5-sulfamoylbenzoyl chloride in 100 ml of ethyl acetate is added dropwise, whilst keeping the mixture at the boil, and the resulting mixture is boiled for a further 2 hours under a reflux condenser. After cooling to room temperature, the reaction mixture is poured into a mixture of 15 g of concentrated sulfuric acid, 200 ml of water and 300 ml of ethyl acetate and extracted, the organic phase is separated off and the aqueous phase is twice more extracted by shaking with ethyl acetate. The product phase is dried over magnesium sulfate, the solvent is distilled off and the oily residue (diethyl 2'-methyl-5'-sulfamoylbenzoyl-malonate) is further processed without any further purification operation.

The 2'-methyl-5'-sulfamoylbenzoyl-malonate obtained as an oil is slowly warmed to 110° C. and the dropwise addition of 18 ml of 85% strength phosphoric acid is started when the temperature reaches about 80° C. The reaction mixture is warmed until the evolution of $CO_2$ has ceased and is then heated at 110° C. for a further half hour. After cooling, about 200 ml of water are added, the resulting mixture is extracted several times with ethyl acetate, the combined organic phases are washed with water and dried over $MgSO_4$, the solvent is driven off, diisopropyl ether is added to the residue and the crystals are filtered off. Crystals with a melting point of 115°-117° C.

The sulfamoylacetophenone derivatives listed below are prepared in an analogous manner: 2'-methyl-5'-dimethylsulfamoyl-acetophenone, melting point 54°-56° C., 3'-methyl-5'-sulfamoyl-acetophenone, melting point 165°-168° C., 3'-methyl-5'-dimethylsulfamoyl-acetophenone, melting point 106°-109° C., 2'-chloro-5'-sulfamoyl-acetophenone, melting point 114°-116° C., 2'-chloro-5'-dimethylsulfamoyl-acetophenone, melting point 79° C., 2'-chloro-5'-methylsulfamoyl-acetophenone, melting point 74°-75° C., 3'-chloro-5'-dimethylsulfamoyl-acetophenone, melting point 100°-102° C. and 2'-bromo-5'-dimethylsulfamoyl-acetophenone, melting point 97°-99° C.

3-Sulfamoylbenzoyl chlorides

Obtained by refluxing the corresponding sulfamoyl-benzoic acid derivatives in an approximately 15 to 20-fold excess of thionyl chloride until the evolution of HCl has ceased and then distilling off the thionyl chloride.

The compounds listed below have been prepared in this way: 2-methyl-5-sulfamoylbenzoyl chloride, melting point 160°-161° C., 2-methyl-5-dimethylsulfamoyl-benzoyl chloride, melting point 84°-89° C., 3-methyl-5-sulfamoylbenzoyl chloride, melting point 152°-155° C., 3-methyl-5-dimethylsulfamoylbenzoyl chloride, melting point 72° C., 2-chloro-5-sulfamoylbenzoyl chloride, melting point 114°-116° C., 2-chloro-5-dimethylsulfamoylbenzoyl chloride, melting point 79° C., 2-chloro-5-methylsulfamoylbenzoyl chloride, melting point 74°-75° C., 3-chloro-5-dimethylsulfamoylbenzoyl chloride, melting point 74°-76° C. and 2-bromo-5-dimethylsulfamoylbenzoyl chloride.

Sulfamoylbenzoic acids

Obtained by introducing the corresponding chlorosulfonylbenzoic acids into an ethanolic solution containing at least 3 moles of the amine $HNR^6R^7$ at room temperature: 2-bromo-5-dimethylbenzoic acid, melting point 174°-176° C., 3-chloro-5-dimethylbenzoic acid, melting point 155°-156° C., 3-methyl-5-sulfamoylbenzoic acid, melting point 258°-262° C., 3-methyl-5-dimethylsulfamoylbenzoic acid, melting point 157°-162° C., 2-methyl-5-sulfamoylbenzoic acid, melting point 247°-251° C., 2-methyl-5-dimethylsulfamoylbenzoic acid, melting point 173°-175° C., 2-chloro-5-dimethylsulfamoylbenzoic acid, melting point 170° C. and 2-chloro-5-methylsulfamoylbenzoic acid, melting point 174° C.

The corresponding chlorosulfonylbenzoic acids are obtained in a manner which is in itself known, by heating the benzoic acids with chlorosulfonic acids at 120° to 165° C. and then decomposing the reaction mixture, after cooling, by adding dropwise to an ice/water mixture: 2-methyl-5-chlorosulfonylbenzoic acid, melting point 151°-155° C., 3-methyl-5-chlorosulfonylbenzoic acid, melting point 176°-180° C., 3-chloro-5-chlorosulfonylbenzoic acid and 2-bromo-5-chlorosulfonylbenzoic acid.

TABLE 5 shows some of the thioureas III prepared; these were obtained by methods known from the literature (compare, for example, Houben-Weyl, "Methoden der organischen Chemie" ("Methods of Organic Chemistry"), Volume 9, page 884, 4th edition, Georg-Thieme-Verlag, Stuttgart, 1955).

| $R^1$ | $R^2$ | $R^3$ | $R^4$ | Melting point (°C.) |
|---|---|---|---|---|
| Me | 2-Cl | 4-Cl | 5-Me | 132 |
| Hex | H | H | H | 77 |
| c-Prop | H | H | H | 124 |
| Me | —O—CH$_2$—O— | | H | 133 |
| Me | —O—(CH$_2$)$_2$—O— | | H | 173 |
| Me | 3-NMe$_2$ | H | H | 133 |
| Me | 4-CF$_3$ | H | H | 145 |
| Me | 3-MeO | 4-MeO | 5-MeO | 167 |
| Me | 2-MeO | 4-MeO | 5-Cl | 193 |
| Me | 2-EtO | 5-Me | H | 111 |
| Me | 2-MeO | 4-Me | 5-Me | 135 |
| Me | 2-Cl | H | H | 146 |
| Me | 4-F | H | H | 93 |
| Me | 2-Me | 4-Me | H | 153 |
| Me | 2-Me | 4-Cl | | 127 |
| Et | 2-Me | H | H | 66 |

We claim:
1. Thiazoline derivative of the formula

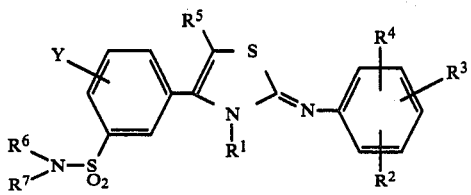

in which R¹ denotes alkyl of 1 to 8 carbon atoms, cycloalkyl of 3 to 8 carbon atoms or alkenyl of 3 to 4 carbon atoms; $R^2$, $R^3$ and $R^4$ are identical or different and denote hydrogen, halogen, alkyl or alkoxy of 1 to 4 carbon atoms, dimethyl- or diethyl-amino or trifluoromethyl, or any two of $R^2$, $R^3$ and $R^4$ together denote methylenedioxy or ethylenedioxy; $R^5$ denotes hydrogen or alkyl of 1 to 3 carbon atoms; $R^6$ denotes hydrogen or alkyl of 1 to 6 carbon atoms; $R^7$ denotes hydrogen, alkyl of 1 to 12 carbon atoms, cycloalkyl of 3 to 12 carbon atoms, allyl, phenethyl or a benzyl of the formula

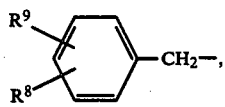

in which $R^8$ and $R^9$ are identical or different and denote hydrogen, methyl, chlorine or methoxy, or $R^6$ and $R^7$ together represent an alkylene chain which can be branched and has a total of up to 8 carbon atoms and in which one methylene group can be replaced by —O— or

and Y denotes hydrogen, halogen or alkyl of 1 to 3 carbon atoms; an alkali or alkaline earth mtal salt thereof, or an acid addition salt thereof with a pharmacologically acceptable acid.

2. Compound of the formula

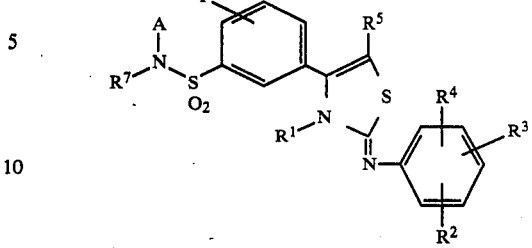

in which $R^1$ to $R^5$, $R^7$ and Y are as defined in claim 1 and A denotes the cation of an alkali metal or alkaline earth metal.

3. 4-(4-Chloro-3-dimethylsulfamoylphenyl)-3-methyl-2-phenylimino-4-thiazoline.

4. 4-(4-Chloro-3-diethylsulfamoylphenyl)-3-methyl-2-phenylimino-4-thiazoline.

5. 4-(4-Chloro-3-dimethylsulfamoylphenyl)-2-(2-chlorophenylimino)-3-methyl-4-thiazoline.

6. 4-(4-Chloro-3-dimethylsulfamoylphenyl)-3-methyl-2-(2-methylphenylimino)-4-thiazoline.

7. 4-(4-Chloro-3-dimethylsulfamoylphenyl)-3-methyl-2-(2,4-dimethylphenyl-imino)-4-thiazoline.

8. 4-(2-Chloro-5-dimethylsulfamoylphenyl)-3-methyl-2-phenylimino-4-thiazoline.

9. 4-(3-Chloro-5-dimethylsulfamoylphenyl)-3-methyl-2-phenylimino-4-thiazoline.

10. 4-(4-Chloro-3-dimethylsulfamoylphenyl)-2-(4-methoxyphenylimino)-3-methyl-4-thiazoline.

11. 4-(4-Chloro-3-sulfamoylphenyl)-3-methyl-2-phenylimino-4-thiazoline.

12. Hypolipidaemic compositions containing a hypolipidaemically effective amount of a compound as defined in claim 1 and a pharmacologically acceptable excipient therefor.

13. Process for the treatment of a lipid metabolism disorder which comprises administering to a patient suffering therefrom a hypolipidaemically effective amount of a compound as defined in claim 1.

* * * * *